(12) United States Patent
Light et al.

(10) Patent No.: US 8,975,302 B2
(45) Date of Patent: Mar. 10, 2015

(54) POLYMER PARTICLES, NUCLEIC ACID POLYMER PARTICLES AND METHODS OF MAKING AND USING THE SAME

(75) Inventors: David Light, New Haven, CT (US); Barnett Rosenblum, San Jose, CA (US)

(73) Assignee: Life Technologies Corporation, Carlsbad, CA (US)

( * ) Notice: Subject to any disclaimer, the term of this patent is extended or adjusted under 35 U.S.C. 154(b) by 192 days.

(21) Appl. No.: 13/543,642

(22) Filed: Jul. 6, 2012

(65) Prior Publication Data
US 2013/0012658 A1 Jan. 10, 2013

Related U.S. Application Data

(60) Provisional application No. 61/505,166, filed on Jul. 7, 2011.

(51) Int. Cl.
*B01F 3/08* (2006.01)
*C12Q 1/68* (2006.01)
*C08F 2/32* (2006.01)
*C08F 220/56* (2006.01)

(52) U.S. Cl.
CPC .............. *C12Q 1/6869* (2013.01); *C08F 2/32* (2013.01); *C08F 220/56* (2013.01); *C12Q 1/6834* (2013.01)
USPC .......... 516/21; 525/375; 526/207; 526/218.1; 526/219.5; 526/219.6; 526/341

(58) Field of Classification Search
USPC .......... 516/21; 526/207, 218.1, 219.5, 219.6, 526/341
See application file for complete search history.

(56) References Cited

U.S. PATENT DOCUMENTS

| | | | |
|---|---|---|---|
| 4,485,224 A | 11/1984 | Smith | |
| 4,918,123 A | 4/1990 | Yang et al. | |
| 5,055,390 A | 10/1991 | Weaver et al. | |
| 5,478,893 A | 12/1995 | Ghosh et al. | |
| 5,785,832 A | 7/1998 | Chiari et al. | |
| 5,795,926 A | 8/1998 | Niessner et al. | |
| 5,932,711 A | 8/1999 | Boles et al. | |
| 6,180,770 B1 | 1/2001 | Boles et al. | |
| 6,372,813 B1 | 4/2002 | Johnson et al. | |
| 6,586,176 B1 | 7/2003 | Trnovsky et al. | |
| 6,656,725 B2 | 12/2003 | Mirzabekov et al. | |
| 2004/0143039 A1* | 7/2004 | Hollomon et al. | 524/35 |
| 2010/0304982 A1 | 12/2010 | Hinz et al. | |

FOREIGN PATENT DOCUMENTS

| | | |
|---|---|---|
| GB | 1440168 | 6/1976 |
| WO | 2004/052942 | 6/2004 |

OTHER PUBLICATIONS

Adessi, C et al., "Solid Phase DNA Amplification: characterisation of primer attachment and amplification mechanisms", *Nucleic Acids Research*, vol. 28, No. 20, e87, 2000, 1-8.

Brenner, Sydney et al., "In vitro cloning of complex mixtures of DNA on microbeads: Physical separation of differentially expressed cDNAs", *PNAS*, vol. 97, No. 4, 2000, 1665-1670.
Chrambach, "The Practice of Quantitative Gel Electrophoresis", *VCH*, Deerfield Beach, 1985.
Elaissari, et al., "Colloidal Polymers: Synthesis and Characterization" *Marcel Dekker, Inc.*, New York, 2003.
Holmes, Diana et al., "Estimation of polyacrylamide gel pore size from Ferguson plots of normal and anomalously migrating DNA fragments", *Electrophoresis*, 12, 1991, 253-263.
Kenney, Mary et al., "Mutation Typing Using Electrophoresis and Gel-Immobilized Acrydite™ Probes", *Biotechniques*, 25, 1998, 516-521.
Marguiles, et al., "Genome Sequencing in Microfabricated High-Density Picolitre Reactors", *Nature*, vol. 437, No. 7057, 2005, 376-380.
Mitra, R et al., "Fluorescent In Situ Sequencing on Polymerase Colonies" , *Anal Biochem.* vol. 320, 2003, pp. 55-65.
Mitra, R, "In situ localized amplification and contact replication of many individual DNA molecules", *Nuc Acids Res*, vol. 27(24), 1999, e34, pp. i-vi.
Rehman, F. et al., "Immobilization of Acrylamide-modified Oligonucleotides by Co-polymerization", *Nucleic Acids Research*, vol. 27, No. 2, 1999, pp. 649-655.
Rickwood, D. et al., "Gel Electrophoresis of Nucleic Acids: A Practical Approach", *IRL Press Limited*, London, 1981.
Righetti, Pier Giorgio et al., "On the Limiting Pore Size of Hydrophilic Gels for Electrophoresis and Isoelectric Focusing", *J. Biochem. Biophys. Methods.* 4, 1981, 347-363.
Saltzman, W. M. et al., "Transport rates of proteins in porous materials with known microgeometry", *Biophys. J.*, 55, 1989, 163-171.
Shapero, Michael et al., "SNP Genotyping by Multiplexed Solid-Phase Amplification and Fluorescent Minisequencing", *Genome Research*, 11, 2001, 1926-1934.
Shendure, J et al., "Accurate Multiplex Polony Sequencing of an Evolved Bacterial Genome", *Science*, vol. 309, 2005, 1728-1732.
Tang, Jing et al., "Polymerizing immobilization of acrylamide-modified nucleic acids and its application", *Biosensors and Bioelectronics*, 24, 2009, 1817-1824.
Xiao, Pengfeng et al., "Gel immobilization of acrylamide-modified single-stranded DNA template for pyrosequencing", *Electrophoresis*, vol. 28, 2007, 1903-1912.

* cited by examiner

Primary Examiner — Robert Jones, Jr.

(57) ABSTRACT

The disclosure relates to methods of making polymer particles, said methods including the steps of: making an aqueous gel reaction mixture; forming an emulsion having dispersed aqueous phase micelles of gel reaction mixture in a continuous phase; adding an initiator oil comprising at least one polymerization initiator to the continuous phase; and performing a polymerization reaction in the micelles. Further, the initiator oil is present in a volume % relative to a volume of the aqueous gel reaction mixture of between about 1 vol % to about 20 vol %. The disclosure also relates to methods of making nucleic acid polymer particles having the same method steps and wherein the aqueous gel reaction mixture includes a nucleic acid fragment, such as a primer.

20 Claims, 13 Drawing Sheets

POLYMER PARTICLES, NUCLEIC ACID POLYMER PARTICLES AND METHODS OF MAKING AND USING THE SAME

CROSS-REFERENCE TO RELATED APPLICATION(S)

This application claims benefit of U.S. Provisional Application No. 61/505,166, filed Jul. 7, 2011, entitled "POLYMER PARTICLES, NUCLEIC ACID POLYMER PARTICLES AND METHODS OF MAKING AND USING THE SAME", and naming inventors David Light and Barnett B. Rosenblum, which is incorporated herein by reference in its entirety.

TECHNICAL FIELD

The disclosure relates to novel methods of making particle compositions having applications in nucleic acid analysis. More specifically, the disclosure relates to methods of making polymer particles.

BACKGROUND

In order to generate sufficient signal for analysis, many applications in genomics and biomedical research utilize the conversion of nucleic acid molecules in a library into separate, or separable, libraries of amplicons of the molecules, e.g. Margulies et al, Nature 437: 376-380 (2005); Mitra et al, Nucleic Acids Research, 27: e34 (1999); Shendure et al, Science, 309: 1728-1732 (2005); Brenner et al, Proc. Natl. Acad. Sci., 97: 1665-1670 (2000); and the like. Several techniques have been used for making such conversions, including hybrid selection (e.g., Brenner et al, cited above); in-gel polymerase chain reaction (PCR) (e.g. Mitra et al, cited above); bridge amplification (e.g. Shapero et al, Genome Research, 11: 1926-1934 (2001)); and emulsion PCR (emPCR) (e.g. Margulies et al, cited above). Most of these techniques employ particulate supports, such as beads, which spatially concentrate the amplicons for enhanced signal-to-noise ratios, as well as other benefits, such as, better reagent access.

These techniques have several drawbacks. In some cases, amplicons are either in a planar format (e.g. Mitra et al, cited above; Adessi et al, Nucleic Acids Research, 28: e87 (2000)), which limits ease of manipulation or reagent access, or the amplicons are on bead surfaces, which lack sufficient fragment density or concentration for adequate signal-to-noise ratios. Another disadvantage of traditional beads is their solid structure and thus lack of diffusivity. Even "macroporous" particles are solid structures that do not diffuse analytes and reporter molecules as quickly or efficiently as gel-based materials. The gel particles have the advantage of increasing diffusivity of analytes and reporter molecules through the gel-based material. This increases the efficiency of moving/ diffusing analytes and reporter molecules, such as, for example, nucleotides being washed over the sensory chip in an apparatus. For example, hydrogen ions and DNA can diffuse through a gel bead with great efficiency regardless of where they are produced and enter the bead because of the gel material. It would also be useful if supports were available that were capable of providing a higher density of analyte binding or attachment sites, particularly for clonal populations of nucleic acid fragments, thereby allowing production of supports with higher template loads.

Gels have been widely used as supports in analytical and synthetic processes and as encapsulating agents, e.g. Weaver et al, U.S. Pat. No. 5,055,390; Tmovsky et al, U.S. Pat. No. 6,586,176, and have interiors accessible to analytical reagents. However, such particulates are limited in that they are typically produced with widely varying size distributions, particularly at lower size ranges, e.g. less than about 30 µm, which makes them unsuitable for many exacting analytical applications, such as large scale DNA sequencing.

U.S. Patent Application Publication No. 2010/0304982, however, describes methods and compositions for making porous microparticles or polymer particles, which may be readily loaded with analytes, such as amplicons of nucleic acid fragments.

There exists a desire, however, for methods of making polymer particles and scaffold nucleic acid polymeric particles (SNAPPs) that are time or cost efficient and also for methods that are capable of producing a high yield of particles, which may also be of high or consistent quality. There also exists a desire for methods of making SNAPPs of high sequencing quality. The inventors have now discovered such novel methods of making polymer particles and SNAPPs and the products produced therefrom.

In the following description, various aspects and embodiments of the invention will become evident. In its broadest sense, the invention could be practiced without having one or more features of these aspects and embodiments. Further, these aspects and embodiments are exemplary. Additional objects and advantages of the invention will be set forth in part in the description which follows, and in part will be obvious from the description, or may be learned by practicing the invention. The objects and advantages of the invention will be realized and attained by means of the elements and combinations particularly pointed out in the appended claims.

SUMMARY

The disclosure relates to novel methods of making particle compositions having applications in nucleic acid analysis. More specifically, the disclosure relates to methods of making polymer particles, said methods comprising the steps of: making an aqueous gel reaction mixture; forming an emulsion comprising dispersed aqueous phase micelles of gel reaction mixture in a continuous phase; adding an initiator oil comprising at least one polymerization initiator to the continuous phase; and performing a polymerization reaction in the micelles. Further, the initiator oil is present in a volume % relative to a volume of the aqueous gel reaction mixture of between about 1 vol % to about 20 vol %. The disclosure also relates to methods of making SNAPPs comprising the same method steps and wherein the aqueous gel reaction mixture comprises a nucleic acid fragment.

The disclosure also relates to polymer particles made by the methods set forth herein, including, but not limited to, polyacrylamide polymer particles and SNAPPs, and methods of using the same.

BRIEF DESCRIPTION OF THE FIGURES

The accompanying drawings are included to provide a further understanding of the invention, and are incorporated in and constitute a part of this specification. The drawings are not intended to be restrictive of the invention as claimed, but rather are provided to illustrate exemplary embodiments of the present teachings and, together with the description, serve to explain certain principles. In the drawings.

DESCRIPTION OF EXEMPLARY EMBODIMENTS

Figure 1:
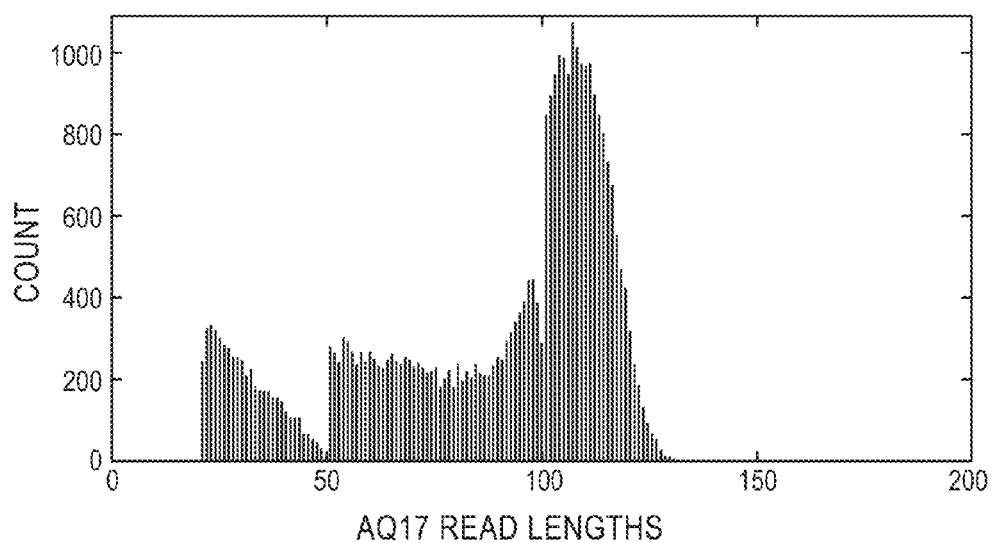
FIG. 1 depicts the counts for the AQ17 read lengths produced in accordance with an embodiment of the disclosure.

The disclosure relates to novel methods of making particle compositions having applications in nucleic acid analysis. More specifically, the disclosure relates to methods of making polymer particles. As used herein, the term "polymer particles," "polymer network," "porous microparticle," and variations thereof, may be used interchangeably and are intended to mean a structure comprising covalently connected subunits, such as monomers, crosslinkers, and the like, in which all such subunits are connected to every other subunit by many paths through the polymer phase, and wherein there are enough polymer chains bonded together (either physically or chemically) such that at least one large molecule is coextensive with the polymer phase, i.e. the structure is above its gel point. In various embodiments, the polymer particles may have a volume in the range of from about 65 aL to about 15 pL, or from about 1 fL to about 1 pL.

The polymer networks of the disclosure include those set forth in U.S. Patent Application Publication No. 2010/0304982 A2, which is incorporated herein by reference. Design factors for making polymer networks may include, but are not limited to, the following: (i) the polymers of the networks are hydrophilic, (ii) they are capable of having a pore or network structure (e.g., average pore diameter, tortuosity, and the like) that permits interior access to various enzymes, especially polymerases, as well as the rapid diffusion of analytes such as, for example, nucleotides and hydrogen ions and (iii) they are physically and chemically stable under conditions where biomolecules, such as enzymes, are functional. There is guidance in the art for selecting polymers and polymerization methodologies to produce polymer networks meeting such performance criteria, such as the following exemplary references, which are incorporated by reference: Saltzman and Langer, J. Biophys., 55:163 (1989); Ghosh et al, U.S. Pat. No. 5,478,893; Mirzabekov, U.S. Pat. No. 6,656,725; Johnson et al, U.S. Pat. No. 6,372,813; Tang and Xiao, Biosensors and Bioelectronics, 24: 1817-1824 (2009); Boles et al, U.S. Pat. Nos. 5,932,711 and 6,180,770; Xiao et al, Electrophoresis, 28: 1903-1912 (2007); Holmes et al, Electrophoresis, 12: 253-263 (1991); Shapero et al, Genome Research, 11: 1926-1934 (2001); Righetti et al, J. Biochem. Biophys. Methods, 4: 347-363 (1981); Mitra et al, Nucleic Acids Research, 27: e34 (1999); Rehman et al, Nucleic Acids Research, 27: 649-655 (1999); Smith, U.S. Pat. No. 4,485,224; Chiari et al, U.S. Pat. No. 5,785,832; Rickwood and Hames, Editors, Gel Electrophoresis of Nucleic Acids (IRL Press, Oxford, 1982); Chrambach, The Practice of Quantitative Gel Electrophoresis (VCH, Deerfield Beach, 1985); Mitra et al, Anal. Biochem., 320: 55-65 (2003); Kenney et al, Biotechniques, 25: 516 (1998); Elaissari, editor, Colloidal Polymers: Synthesis and Characterization (Marcel Dekker, Inc., New York, 2003); and the like.

In at least one exemplary embodiment, the polymer network may comprise polyacrylamide gels. Polyacrylamide gels may be formed by copolymerization of acrylamide and bis-acrylamide ("BIS," N,N'-methylene-bisacrylamide). The reaction is a vinyl addition polymerization initiated by a free radical-generating system. In a standard nomenclature for forming polyacrylamide gels, T represents the total percentage concentration (w/v, in mg/mL) of monomer (acrylamide plus crosslinker) in the gel. The term C refers to the weight percentage of the total monomer represented by the crosslinker. For example, an 8%, 19:1 (acrylamide/bisacrylamide) gel would have a T value of 8% and a C value of 5%.

In various exemplary embodiments, the polymer networks may comprise polyacrylamide gels with total monomer percentages in the range of from about 3% to about 20%, such as in the range of from about 5% to about 10%. In various exemplary embodiments, the crosslinker percentage of monomers may be in the range of from about 5% to about 20%. In additional exemplary embodiments, polymer networks may comprise about 10% total acrylamide, of which about 10% may be bisacrylamide.

Accordingly, in at least one aspect of the disclosure, the polyacrylamide particle composition may comprise a population of polyacrylamide particles with an average particle size of less than about 15 µm, for example less than about 10 µm, or less than about 5 µm, such as 1.5 µm. The polyacrylamide particles may have a coefficient of variation of less than about 20%, for example less than about 15%. In one embodiment, the polyacrylamide particles may have a weight:volume percentage of about 25% or less. In another embodiment, the polyacrylamide particles may be spheroidal and have an average diameter of less than about 15 µm with a coefficient of variation of less than about 20%.

The disclosed methods of making polymer particles comprise the steps of: making an aqueous gel reaction mixture; forming an emulsion comprising dispersed aqueous phase micelles of gel reaction mixture in a continuous phase; adding an initiator oil comprising at least one polymerization initiator to the continuous phase; and performing a polymerization reaction in the micelles. In further embodiments, the initiator oil is present in a volume % relative to a volume of the aqueous gel reaction mixture of between about 1 vol % to about 20 vol %. As used herein, the term "aqueous gel reaction mixture," and variations thereof, is intended to mean an aqueous solution of monomers and optionally additional components that polymerize under appropriate conditions to form a polymer particle or network as described above. For example, the aqueous gel reaction mixture may contain a crosslinker as an optional additional component.

It is within the ability of one of ordinary skill in the art to select monomers for use in the aqueous gel reaction mixture in accordance with the desired result, including the criteria set forth above, in order to form the polymer networks described herein. In one exemplary embodiment, the aqueous gel reaction mixture may include acrylamide as the monomer. In other exemplary embodiments, the aqueous gel reaction may include other polymeric compounds, for example, methacrylates, vinyls, and acrylamide derivatives, such as, for example, hydroxyethyl acrylamide. Optional additional components include at least one kind of nucleic acid fragment. Nucleic acid fragments of the disclosure include, but are not limited to, nucleic acid primers and DNA fragments from a library, non-limiting examples of which are set forth in U.S. Patent Application Publication No. 2010/0304982 A1. When a nucleic acid fragment is present, the polymer particle may also be referred to as a scaffolded nucleic acid polymer particle ("SNAPP"), non-limiting examples of which are also set forth in U.S. Patent Application Publication No. 2010/0304982 A1.

In various embodiments, the aqueous gel reaction mixture may be made by dissolving the monomers and optional additional components in water, such as for example, by combining the monomers with a sufficient amount of water in a conical tube and vortexing the mixture until the monomers are dissolved. When additional components are present in the aqueous gel reaction mixture, they may be dissolved simultaneously with the monomers or separately, either before or after the monomers.

An emulsion comprising dispersed aqueous phase micelles of gel reaction mixture in a continuous phase is then formed. The emulsion may be formed by dispensing the aqueous gel reaction mixture into a continuous phase while stirring to form droplets or micelles.

The continuous phase of the emulsion may comprise at least one oil and at least one surfactant. Examples of oils for use in the continuous phase include, but are not limited to, mineral oil and diethylhexyl carbonate, such as that marketed under the trade name TEGOSOFT DEC® by EVONIK Goldschmidt GmbH of Germany, poly(dimethylsiloxane) by Fisher Scientific, and heptane by Sigma-Aldrich. Surfactants for use in the continuous phase include, but are not limited to cetyldimethiconecopolyol, such as that marketed under the trade name Abil WE09® by EVONIK Goldschmidt GmbH of Germany, as well as any heat stable silicone surfactants and dimethicone derivatives, such as, for example, PEG-10 Dimethicone, marketed under the trade name GRANSURF by Grant Industries.

In various embodiments, the emulsion may be degassed after formation. By way of example only, degassing may be performed by gently sparging the emulsion with moistened argon.

An initiator oil comprising at least one polymerization initiator is then added to the continuous phase. The initiator oil may be a saturated solution of the polymerization initiator in an oil. Examples of polymerization initiators include, but are not limited to, oil soluble polymerization initiators such as Azobisisobutyronitrile (AIBN) and those set forth in U.S. Patent Application Publication No. 2010/0304982 A2, including those in Table II. In at least one embodiment, the polymerization initiator may be AIBN. Examples of the oils for use in the initiator oil include, but are not limited to, mineral oil and diethylhexyl carbonate, such as that marketed under the trade name TEGOSOFT DEC® by EVONIK Goldschmidt GmbH of Germany, poly(dimethylsiloxane) by Fisher Scientific, and heptane by Sigma-Aldrich.

In various exemplary embodiments, the initiator oil is present in a volume % relative to a volume of the aqueous gel reaction mixture of, for example, between about 1 vol % and about 20 vol %. This volume % may adequately sustain polymerization initiator concentration at the oil/water interface during polymerization.

The polymerization reaction is performed in the micelles. The rate of polymerization is independent of temperature; however, the occurrence of a polymerization reaction can be dependent on achieving a temperature at which the initiator compound releases radicals. In various embodiments, the polymerization reaction may be initiated by increasing the temperature of the emulsion to a temperature adequate to initiate polymerization, such as about 50° C. or greater, such as 75° C. or greater, or 90° C. or greater. When nucleic acid fragments are present during the polymerization reaction, the SNAPPs may undergo damage if the polymerization products remain under the conditions of increased temperature after polymerization.

In various embodiments, the methods described herein may comprise quenching the reaction after polymerization. In at least one embodiment, the reaction may be quenched immediately after polymerization. The polymerization reaction can indicate completion, such as for example, by the appearance of particles or a spike in the temperature profile. Quenching the reaction may, in various embodiments, comprise cooling the emulsion to room temperature or lower. In an example, quenching includes cooling the emulsion in a refrigerator or on ice.

The methods of the disclosure may further comprise separating the polymer particles from the continuous phase. In an example, separating is performed by centrifugation.

The disclosure also relates to methods of making SNAPPs. As used herein, the terms "scaffolded nucleic acid polymer particles," "nucleic acid polymer particles," and "SNAPPs," are intended to mean polymer particles and covalently attached copies of at least one kind of nucleic acid fragment. In various embodiments, the SNAPPs may comprise at least two kinds of nucleic acid fragments.

As set forth above, nucleic acid fragments of the disclosure include, but are not limited to, nucleic acid primers and DNA fragments from a library, non-limiting examples of which are set forth in U.S. Patent Application Publication No. 2010/0304982 A1. In at least one embodiment, the nucleic acid fragment may be a nucleic acid primer. Any suitable primer that is known to one of skill in the art may be selected for use with the disclosure. By way of example only, primers labeled A Primer and B Primer have been used to illustrate certain exemplary embodiments throughout the disclosure and within the exemplary methods disclosed herein. In other exemplary embodiments, various alternative methods may be used for amplifying DNA onto the beads.

Non-limiting examples of SNAPPs are set forth in U.S. Patent Application Publication No. 2010/0304982 A1.

In at least one exemplary embodiment, the SNAPPs may comprise polyacrylamide gels. In accordance with the description above, in at least one aspect of the disclosure, the SNAPPs may comprise a population of polyacrylamide particles with an average particle size of less than about 15 µm, for example less than about 10 µm, or less than about 5 µm, such as 1.5 µm. The polyacrylamide particles may have a coefficient of variation of less than about 20%, for example less than about 15%. In another embodiment, the polyacrylamide particles may be spheroidal and have an average diameter of less than about 15 µm with a coefficient of variation of less than about 20%.

The disclosed methods of making SNAPPs comprise the steps of: making an aqueous gel reaction mixture comprising at least one nucleic acid fragment; forming an emulsion comprising dispersed aqueous phase micelles of gel reaction mixture in a continuous phase; adding an initiator oil comprising at least one polymerization initiator to the continuous phase; and performing a polymerization reaction in the micelles. In further embodiments, the initiator oil is present in a volume % relative to a volume % of the gel reaction mixture of between about 1 vol % to about 20 vol %.

As described above, the aqueous gel reaction mixture is an aqueous solution of monomers and optionally additional components that polymerize under appropriate conditions to form a polymer particle or network as described above. In this embodiment, the aqueous gel reaction mixture further comprises at least one nucleic acid fragment, as described herein.

In various embodiments, the aqueous gel reaction mixture may be made by dissolving the monomers and optional additional components in water, such as for example, by combining the monomers with a sufficient amount of water in a conical tube and vortexing the mixture until the monomers are dissolved. When additional components are present in the aqueous gel reaction mixture, they may be dissolved simultaneously with the monomers or separately, either before or after the monomers.

The nucleic acid fragment may be added to the gel reaction mixture before or after the monomers and optional additional components are dissolved. In a preferred embodiment of the disclosure, particle components, including the nucleic acid fragment, may be added to the gel reaction mixture before polymerization.

An emulsion comprising dispersed aqueous phase micelles of gel reaction mixture in a continuous phase is then formed. The emulsion may be formed by dispensing the aqueous gel reaction mixture into a continuous phase while stirring to form droplets or micelles. The continuous phase of the emulsion may comprise at least one oil and at least one surfactant, as described above.

In various embodiments, the emulsion may be degassed after formation. By way of example only, degassing may be performed by gently sparging the emulsion with moistened argon.

An initiator oil comprising at least one polymerization initiator is then added to the continuous phase. The initiator oil may be a saturated solution of the polymerization initiator in an oil, as described above. In at least one embodiment, the polymerization initiator includes AIBN.

In various exemplary embodiments, the initiator oil is present in a volume % relative to a volume of the aqueous gel reaction mixture of between about 1 vol % to about 20 vol %. This volume % may adequately sustain polymerization initiator concentration at the oil/water interface during polymerization.

Then, the polymerization reaction in the micelles is performed. As described above, polymerization is achieved when the reaction is complete. In various embodiments, the polymerization reaction may be initiated by increasing the temperature of the emulsion to a temperature adequate to initiate polymerization, such as about 50° C. or greater, such as 75° C. or greater, or 90° C. or greater. As described above, the SNAPPs may undergo damage if the polymerization products remain under the conditions of increased temperature after polymerization.

In some embodiments, the methods described herein may comprise terminating the reaction as soon as possible after polymerization. The assays described herein demonstrate that allowing the reaction to proceed for durations beyond the minimum amount of time required for polymerization can increase the amount of primer damage on the nucleic acid polymer products, and thereby decrease the utility of such products. Disclosed herein are methods for determining the minimum time required for polymerization and for terminating the reaction as soon as possible (e.g., via quenching or other methods) after such polymerization is substantially complete.

In various embodiments, the methods described herein may comprise quenching the reaction after polymerization. In at least one embodiment, the reaction may be quenched immediately after polymerization. The point at which the polymerization reaction is complete can be determined, such as for example, by the appearance of particles or a spike in the temperature profile. Quenching the reaction may, in various embodiments, comprise cooling the emulsion to room temperature or lower. Quenching can be performed by, for example, cooling the emulsion in a refrigerator or on ice.

The methods of the disclosure may further comprise separating the SNAPPs from the continuous phase. Separating can include, for example, centrifugation.

In at least one embodiment, the disclosed methods may produce polymer particles or SNAPPs having three-dimensional scaffolds for attaching greater numbers of template molecules than possible with solid beads that have only a two-dimensional surface available for attachment. Additionally, the gel particles have increased superior diffusivity of analytes and reporter molecules such that hydrogen ions and DNA can diffuse through a gel bead with great efficiency, regardless from where they are produced and enter the bead because of the gel material.

In other embodiments, the disclosed methods may produce polymer particles or SNAPPs having shapes with larger surface-to-volume ratios than spherical particles. Such shapes include, for example, tubes, shells, hollow spheres with accessible interiors (e.g. nanocapsules), barrels, multiply connected solids, including doubly connected solids, such as donut-shaped solids and their topological equivalents, triply connected solids and their topological equivalents, four-way connected solids and their topologically equivalents, and the like. Such particles are referred to herein as "non-spheroidal microparticles." Techniques for producing and characterizing such particles are disclosed in Elaissari, editor, Colloidal Polymers: Synthesis and Characterization (Marcel Dekker, Inc., New York, 2003), and like.

In various embodiments, the disclosed methods may produce polymer particles or SNAPPs at a faster rate than methods known in the art, may yield a greater number of particles from a given batch size, or using a smaller amount of polymerization initiator than methods known in the art. In at least one embodiment, the method may produce polymer particles or SNAPPs having a packed density of at least about 5%, such as at least about 10%, at least about 15%, or at least about 20%.

In various embodiments, the disclosed methods may produce SNAPPs with high-quality sequencing read lengths. For example, the SNAPPs may be of the same, longer or shorter read lengths but they may exhibit higher quality reads with fewer errors. In various embodiments, the higher quality reads with few errors may be indicated by the number of bases having an actual Q17 ("AQ17") quality value at a length value of 100 bases or greater or an actual Q20 ("AQ20") quality value at a length value or 100 bases or greater. As is understood by one of skill in the art, the Q17 quality value attributed to a read is an estimate of the total error rate in the read corresponding to a Phred-scale quality score of 17. The Phred scale is defined as 10×log 10(error probability), so Q17 corresponds to an error rate of 2% and Q20 corresponds to an error rate of 1%.

FIG. 1 depicts the counts for the AQ17 (number of reads that reached a given number of base pairs, such as 50 or 100 base pairs, with an error rate less than or equal to 2%) read lengths produced in accordance with an embodiment of the disclosure. As shown by FIG. 1, thousands of the SNAPPs of the disclosed embodiment were found to have two errors or less in every 100 base pairs. The damage to the primers and the amount of errors are reduced when amount of initiator is reduced or SNAPPS are removed from the heat source immediately following completion of the polymerization. As stated above, exposure to heat may damage the nucleic acid fragments; thus, exposure to heat after polymerization may increase the occurrence of damage to the B primer assay. A method for controlling or reducing the amount of damage to the beads may be by controlling the amount of time the bead is exposed to the heat. In at least one embodiment, the reaction emulsion may be heated until the polymerization reaction is completed and then promptly removed. The length of the polymerization reaction may vary depending on, among other things, the monomers and polymer used in the reaction mixture, other reactants, and the volume of reaction emulsion, but it is within the ability of one of ordinary skill in the art to determine when the polymerization reaction is complete.

Figure 2A:
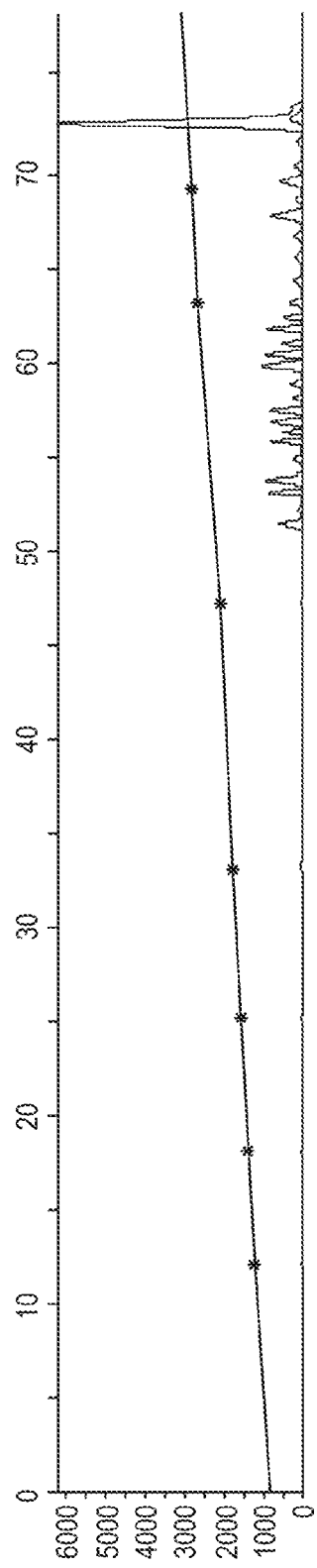
FIGS. 2A-D compare observed levels of primer damage among different SNAPP pools made in accordance with conventional methods (FIGS. 2A-C) with observed levels of primer damage among SNAPP pools made within the scope of the disclosure (FIG. 2D)
Figure 2B:
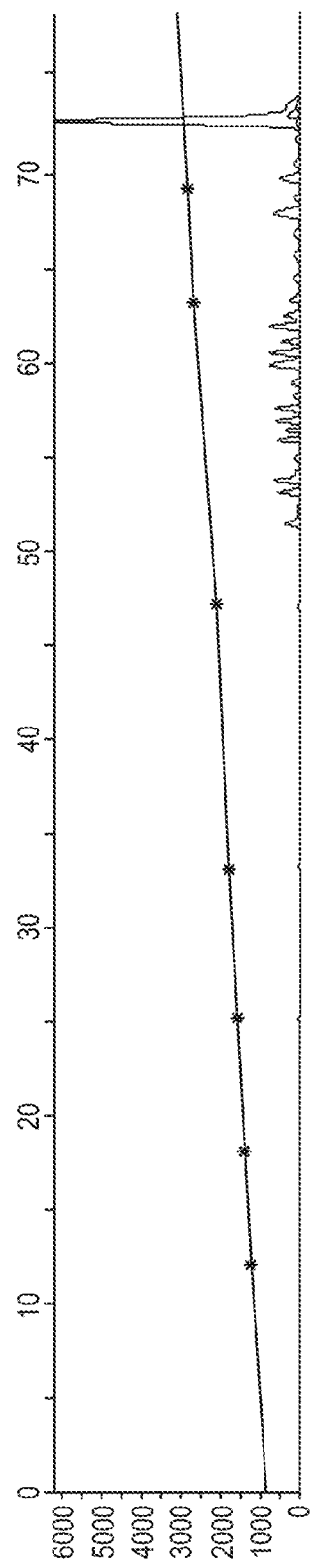
Figure 2C:
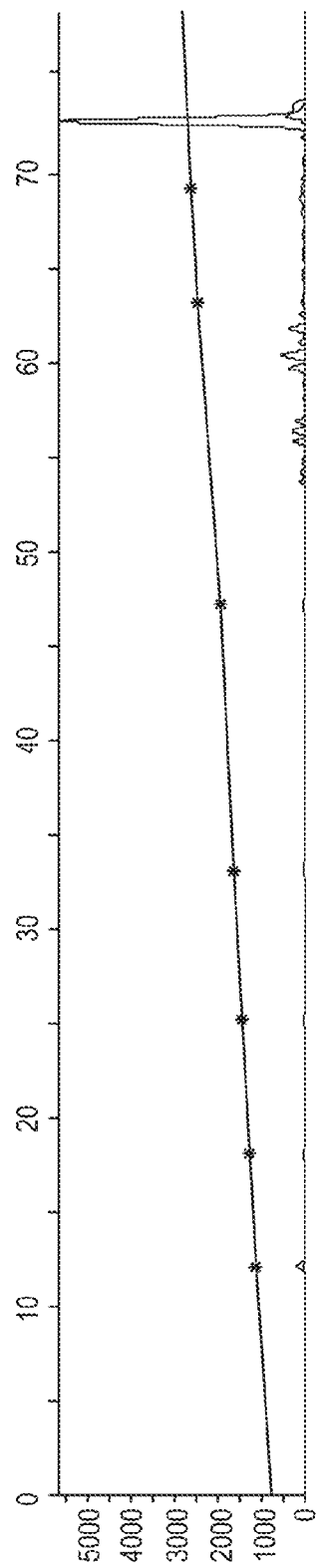
Figure 2D:
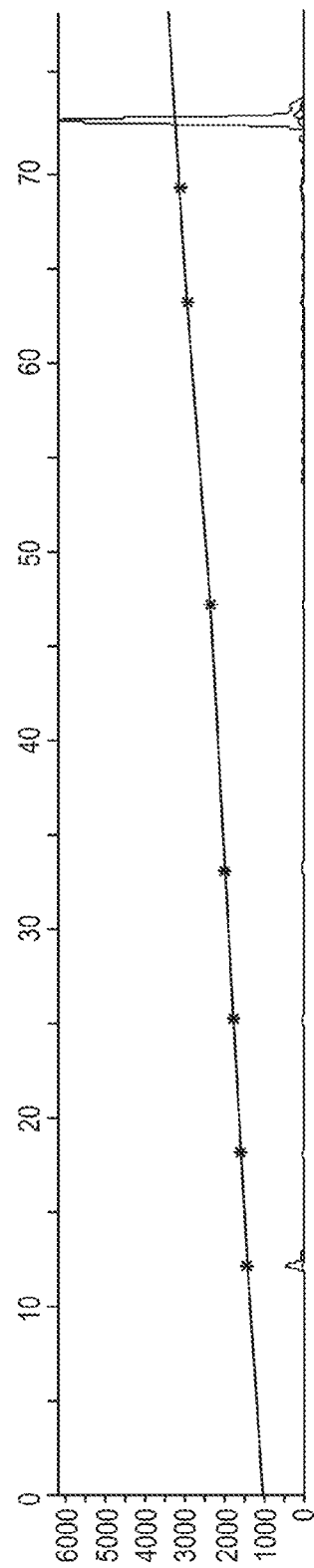

In various embodiments, the disclosed methods may produce SNAPPs with less primer damage over that of SNAPPs not within the scope of the disclosure or made by methods previously known in the art. For example, in FIGS. 2A-D, primer damage is compared between different SNAPP pools made in accordance with the methods outside the scope of the disclosure (FIGS. 2A-C) with SNAPP pools made within the scope of the disclosure (FIG. 2D). The peaks along the horizontal axis indicate the position in the primer of damaged nucleotides in each pool tested while the vertical axis indicates the amount of each peak, including for example, regions of the sequence where the polymerase fell off the strand due to a modified or damaged template nucleotide. FIG. 2D, which depicts the B primer damage from the pool made using a disclosed method, exhibits the least amount of B primer damage comparatively.

In various embodiments, the average length of the sequencing product produced using SNAPPs of the disclosure may be greater than that of the sequencing product produced from SNAPPs not within the scope of the disclosure. In another embodiment, the average B primer region relative to the full length of the sequencing product using SNAPPs of the disclosure may be less than that of the sequencing product produced from SNAPPs not within the scope of the disclosure. In another embodiment, the average B primer region relative to the full length of the sequencing product using SNAPPs of the disclosure may be less than about 2%. In particular, for each of the read lengths disclosed herein (or that is produced from methods of producing SNAPPs disclosed herein), the AQ17 result is of higher quality than that of the sequencing product produced from SNAPPs not within the scope of the disclosure. For example, in Table 1 below, the properties of a SNAPPs produced from an aqueous initiation system are disclosed and may be compared to those of SNAPPs made in accordance with the disclosure, which were produced using an oil-initiated system, as set forth in Table 2 below. The AQ17 values of the systems demonstrate a marked difference in quality between the read lengths at varying sequence lengths. The quality of the oil-initiated system is higher in all three read length samples that were measured for the aqueous- and oil-initiated systems.

TABLE 1

Aqueous Initiated SNAPPs

|  | AQ17 | 100Q17 | 200Q17 |
|---|---|---|---|
| Mean | 29,347,354 | 173,978 | 148,609 |
| CV | 23% | 21% | 23% |
| Rmin90% | 19,359,346 | 119,721 | 99,229 |

TABLE 2

Oil Initiated SNAPPs

|  | AQ17 | 100Q17 | 100Q20 |
|---|---|---|---|
| Mean | 45,400,000 | 322,804 | 284,400 |
| SD | 5,715,476 | 63,167 | 63,440 |
| CV | 13% | 20% | 22% |
| Rmin90% | 36,039,511 | 219,353 | 180,501 |

Additionally, the disclosure relates to the use of the SNAPPs described herein in making amplicon libraries, such as described in U.S. Patent Application No. 2010/0304982.

Additionally, the disclosure relates to methods of measuring the damage incurred by a primer, such as the B primer referred to herein, the damage occurring as a result of incorporating or attaching the primer to a surface. The damaged B primer is manifested by extension products shorter than the full length extension product, but which end in the B primer region based on sequencing of the full extension product. This assay may be applied to any primer fixed to a surface by any method to determine if the primer has been damaged. Each step of the assay results in a unique product such that minimal washing is utilized at each step. Initially a template with a complementary region to the primer is hybridized to the primer, with the template in excess. Following hybridization excess fluid with the excess template is removed. A DNA polymerase in an appropriate buffer, with Mg2+ and nucleotides is added and incubated at an appropriate temperature for the polymerase to extend the surface bound primers the full length of the template. Following the extension, excess fluid is again removed from the surface sample, along with the polymerase, buffer, Mg2+ and nucleotides. A dye labeled primer complementary to the 3' end of the extended template is added and hybridized to the extended surface primer. Excess dye labeled primer and buffer are removed and a DNA polymerase, Mg2+ and nucleotides are added. The sample is again incubated at an appropriate temperature for the DNA polymerase, to extend back toward the primer on the surface. Excess buffer with the DNA polymerase, Mg2+, and nucleotides are removed. The dsDNA is denatured and the supernatant contains the dye labeled product. The products are separated by an electrophoretic method and visualized.

Primer damage is dependent on the manner in which the primer is incorporated into or attached to the surface. Incorporation of a primer during acrylamide polymerization may expose the primer to oxygen radicals which may lead to DNA damage including abasic sites and modified nucleotides. Attaching an oligonucleotide to a surface through an amine coupling at the 5' end of the oligo, may result in additional couplings of the oligonucleotide through the exocyclic amines and likely will appear as damaged DNA in this assay. Increased DNA damage, particularly from oxygen radicals, may result in primer which cannot be extended by the DNA polymerase as well as primers that may be sufficiently damaged that a primer complimentary to the primer on the bead will not hybridize, such that the true total surface primer cannot be quantified.

In some embodiments, the disclosure relates generally to methods, compositions and kits for evaluating the amount of primer damage on a SNAPP particle. Such damage can be evaluated in an assay that determines what proportion of the surface-linked primers are capable of supporting nucleic acid synthesis (where damaged primers typically do not support such synthesis).

For example, in some embodiments the disclosure relates generally to a method for detecting extension of a primer, comprising: forming a primer:template duplex. In some embodiments, such forming a primer:template duplex includes contacting a surface-linked primer with a nucleic acid template, optionally under conditions where the surface-linked primers hybridizes to the nucleic acid template to form the primer:template duplex.

In some embodiments, the method can further include extending the surface-linked primer of the primer:template duplex, thereby forming an extended surface-linked primer.

In some embodiments, the method can further include forming a product:primer duplex (also referred to interchangeably herein as a "primer:primer duplex", which terms are intended to refer interchangeably to a duplex formed via hybridization of a portion of the extended surface-linked primer with a labeled primer). In some embodiments, such forming a product:primer duplex can include contacting the extended surface-linked primer with a labeled primer under conditions where the labeled primer hybridizes to the extended surface primer, thereby forming the product:primer duplex;

In some embodiments, the method can further include extending the labeled primer of the product:primer duplex, thereby forming an extended labeled primer.

In some embodiments, the method can further include detecting the label of the extended labeled primer.

In some embodiments, the method can be performed simultaneously to detect extension of a plurality of primers attached to a surface, optionally to the same surface (e.g., a surface of a SNAPP particle).

For example, in some embodiments the disclosure relates generally to a method for determining the relative proportion of one or more primer extension products within a population of primer extension products, comprising: forming a plurality of primer:template duplexes. Such forming a plurality of primer:template duplexes can further include contacting a plurality of surface-linked primers with a plurality of nucleic acid templates, optionally under conditions where at least two of the surface-linked primers hybridize to different nucleic acid templates.

In some embodiments, the method can further include extending the surface-linked primer of at least two of the plurality of primer:template duplexes, thereby forming a plurality of surface-linked extended primers.

In some embodiments, the method can further include forming a plurality of product:primer duplexes by contacting at least some of the plurality of extended surface-linked primers with a plurality of labeled primers, optionally under conditions where at least two of the extended surface-linked primers hybridize to different labeled primers.

In some embodiments, the method can further include extending the labeled primer of at least two of the plurality of product:primer duplexes, thereby forming a population of extended labeled primers.

In some embodiments, the method can further include separating at least two different members of the population of extended labeled primers from each other.

In some embodiments, the method further includes: separately detecting the at least two different members after the separating.

In some embodiments, the at least two different members of the population include a first extended labeled primer and a second extended labeled primer, and the method further includes separately detecting the label of the first extended labeled primer and the label of the second extended labeled primer.

In some embodiments, the population includes a first extended labeled primer and the method further includes determining the amount of the first extended labeled primer, optionally based on the total amount of signal detected from the label of the first extended labeled primer.

In some embodiments, the population further includes a second extended labeled primer and the method further includes determining the amount of the second extended labeled primer based on the total amount of signal detected from the label of the second extended labeled primer.

Figure 3A:
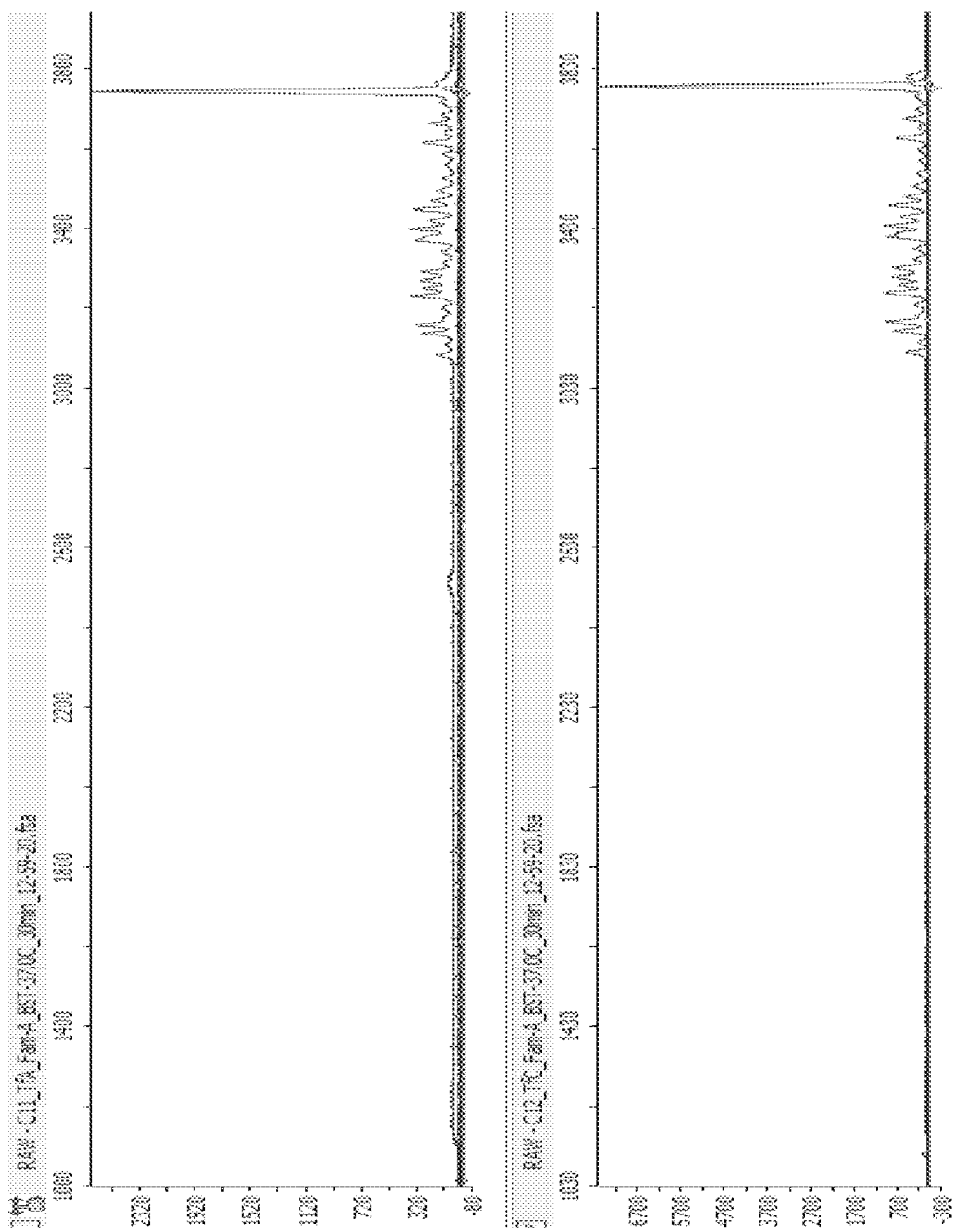
FIGS. 3A-G depicts a comparison of the assays prepared according to the protocol set forth in the disclosure, quantifying DNA primer damage.

In the set of FIGS. 3A-G, the measurements obtained from using the disclosed method are presented as illustrations. For example, FIG. 3A illustrates the Solution Phase Extension of a Primer A on TfA and TfC SNAPPs (i.e., control SNAPPs, which already have an extended B primer and have the complementary region at the 3' end to primer A). In this case, the experiment was started at hybridizing the dye labeled sequencing primer A and then extending back to primer B with polymerase, followed by denaturation and electrophoresis. The products depicted in this figure suggest that these products are in the B primer region. This is made evident by the electropherograms, which show that the extension of different fragments (TfA and TfC) result in the same pattern of incomplete extension products, where the sequences between the primers is different and only the primer sequences are the same.

Figure 3B:
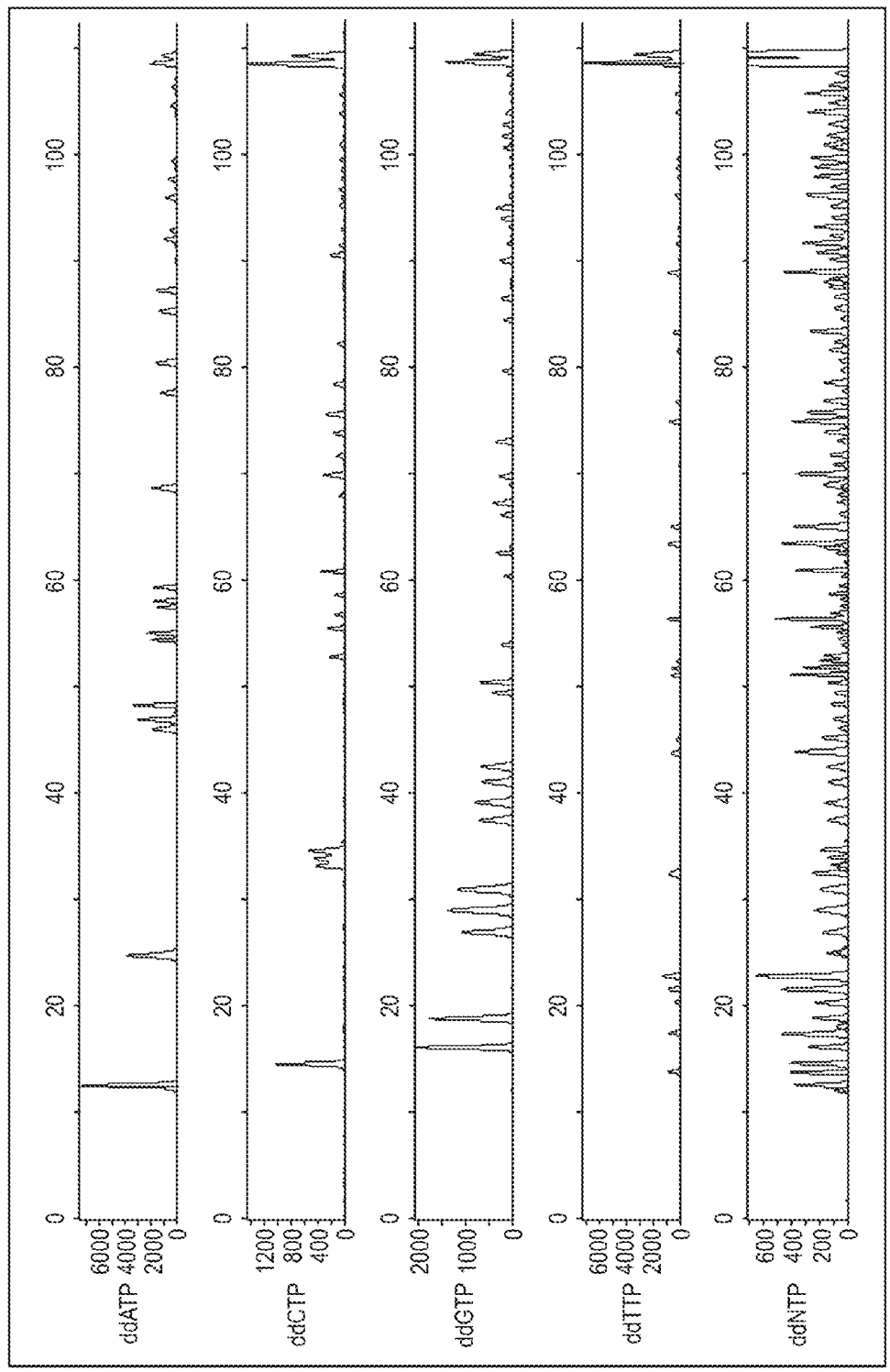

FIG. 3B, depicts a comparison of single dNTP's to the total sequence of nucleotides. Here, sequencing was carried out using TfA with Taq polymerase, Fam-A primer and unlabeled ddNTP's in accordance with the methods described herein. The total ddNTP electropherogram shown in FIG. 3B was prepared by adding the finished sequencing samples, shown in the figure, together. The peaks occurring before the full length product peak are indicative of sites on the B primer where the polymerase fell off or stopped either due to the incorporation of the indicated ddNTP or due to various DNA damage motifs induced by radicals during bead polymerization. Clean peaks, that is, peaks indicating only one base per position were observed in the TfA region of the template, while in the B primer region peaks are seen at each position in each of the ddNTP experiments as the polymerase is falling off the extended product oligonucleotide as a result of damaged nucleotides in the template strand (B primer region) rather than due to the incorporation of a ddNTP in the extended product strand. The lower in magnitude the peaks are, the lower the concentration of damaged primers on the beads.

Figure 3C:
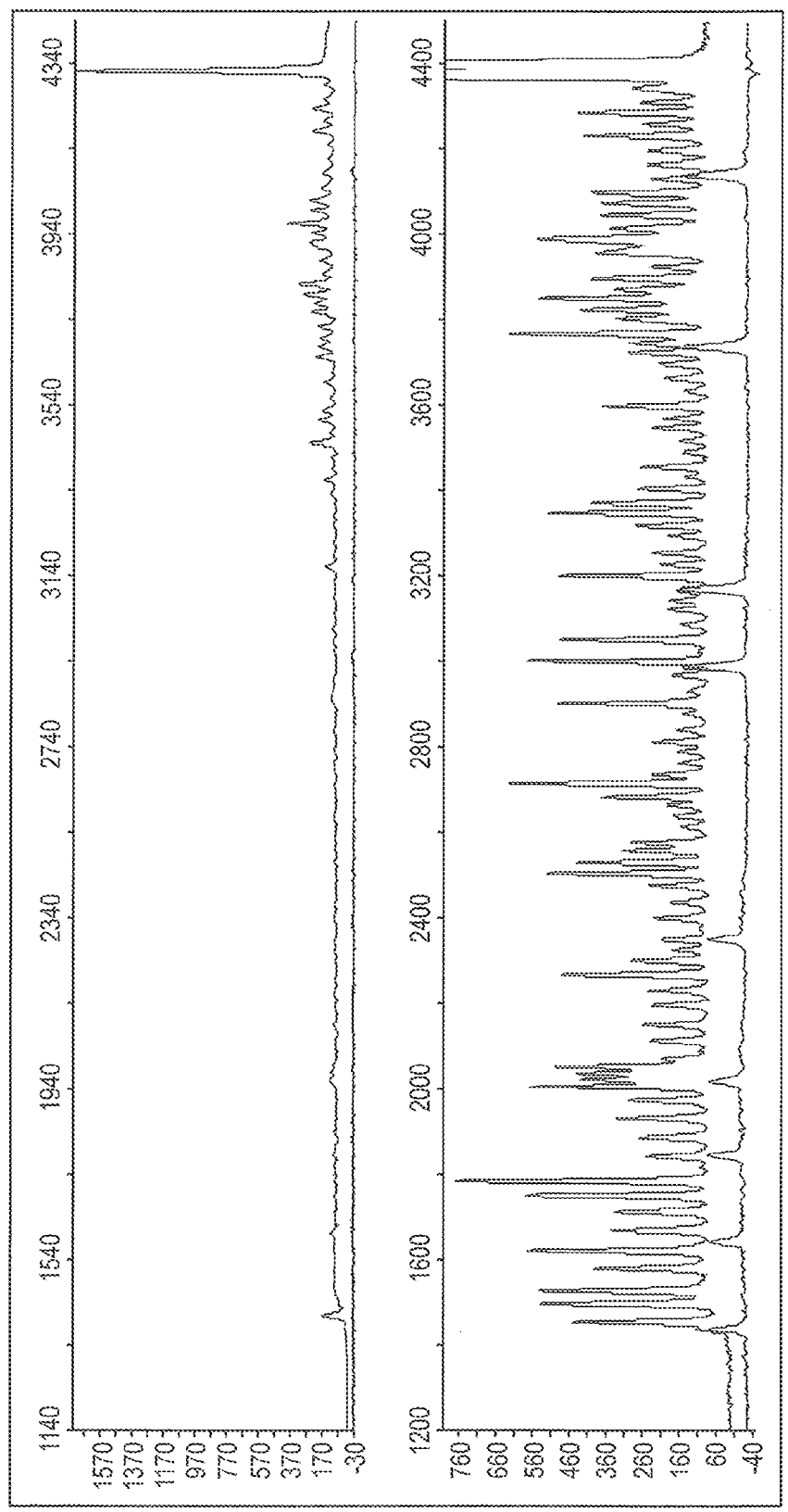
Figure 3D:
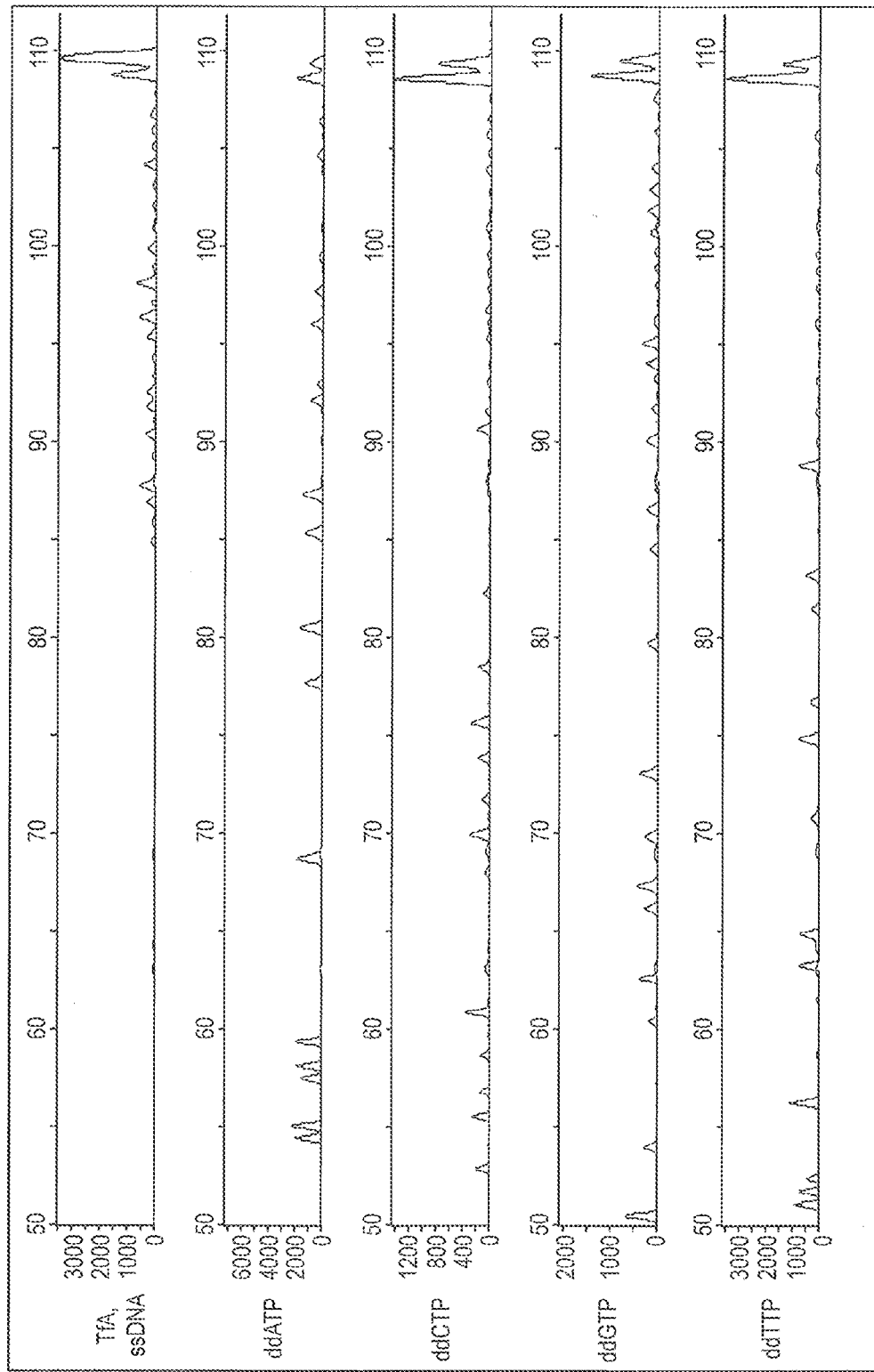
Figure 3E:
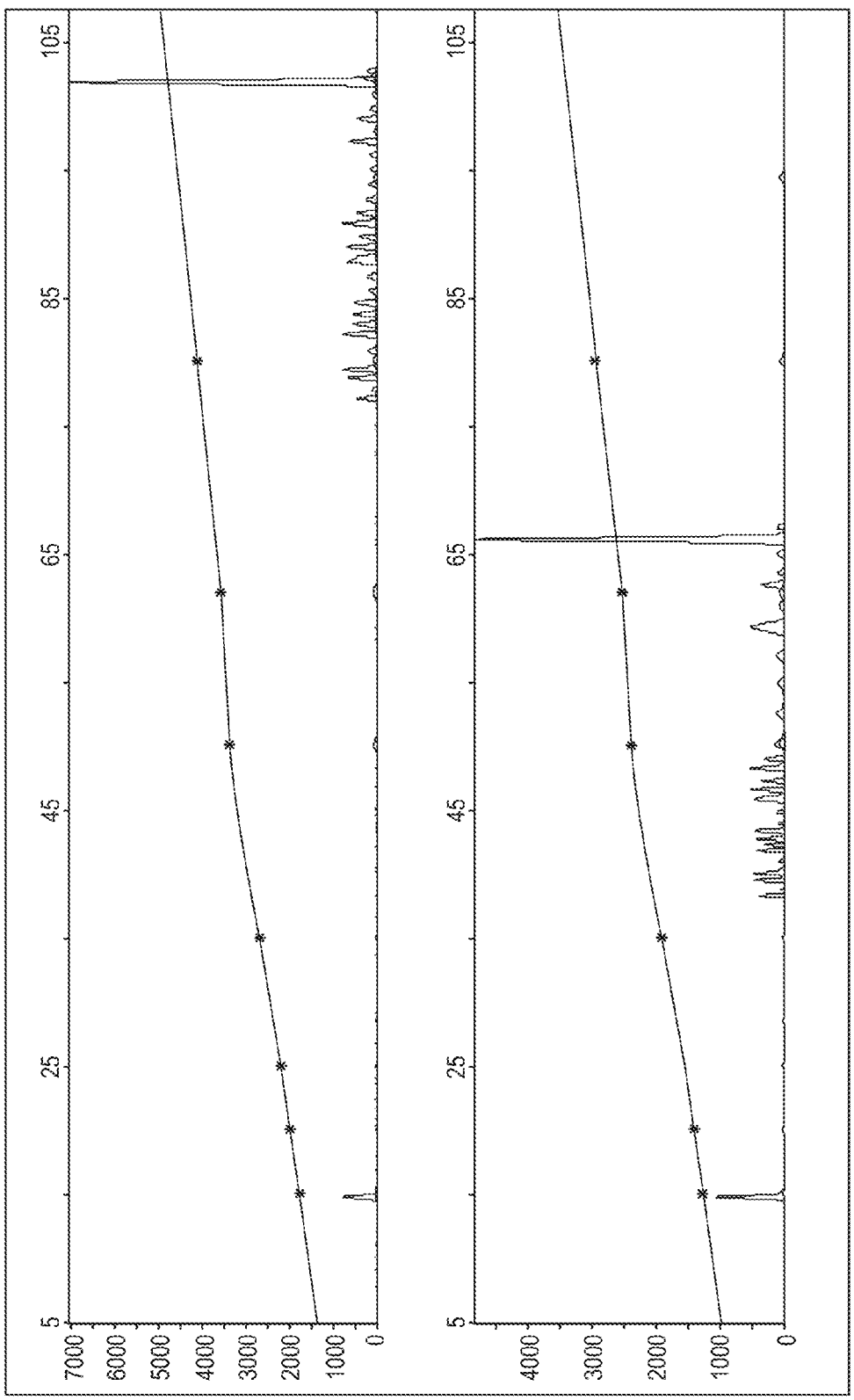

FIG. 3C depicts a comparison of the sequencing extension of TfA with the free dNTP extension of ssTfA with Fam-A primer demonstrating that the region of damaged nucleotides (B primer region) in the free extension experiment corresponds to the region observed in the ddNTP experiment where a sequence cannot be determined because of the fall off of the polymerase due to the damaged nucleotides. The correct number of nucleotide positions are present between the last sequenced base and the full extension peak to account for the bases in the B primer. FIG. 3D depicts the results of the assay measurement showing the alignment of B' primer extension failures on TfA SNAPPs. The last three bases at the 3' end of the B' primer do not show stops on the extension of TfA or TfC SNAPPs, suggesting that these bases are critical for extension from the B primer and must be undamaged. When the extension on SNAPPs with TfC and Template AB were compared, there was no difference observed in the pattern or relative percentage of B primer damage on different Nanomi SNAPPs, regardless of whether they were assayed from Tf-converted SNAPPs or they were assayed following a Hyb extend assay with Template AB (comparison shown in FIG. 3E).

Figure 3F:
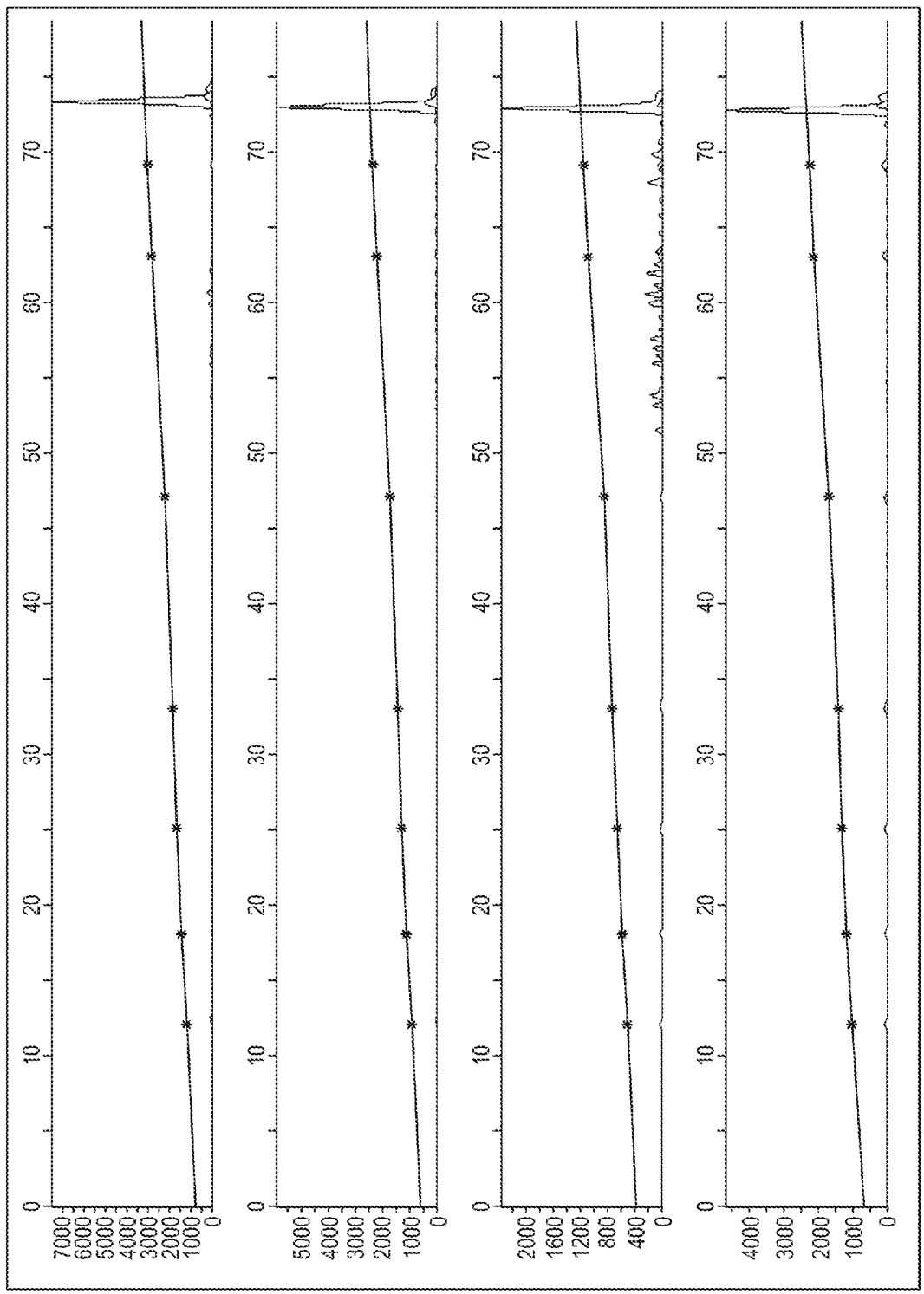
Figure 3G:
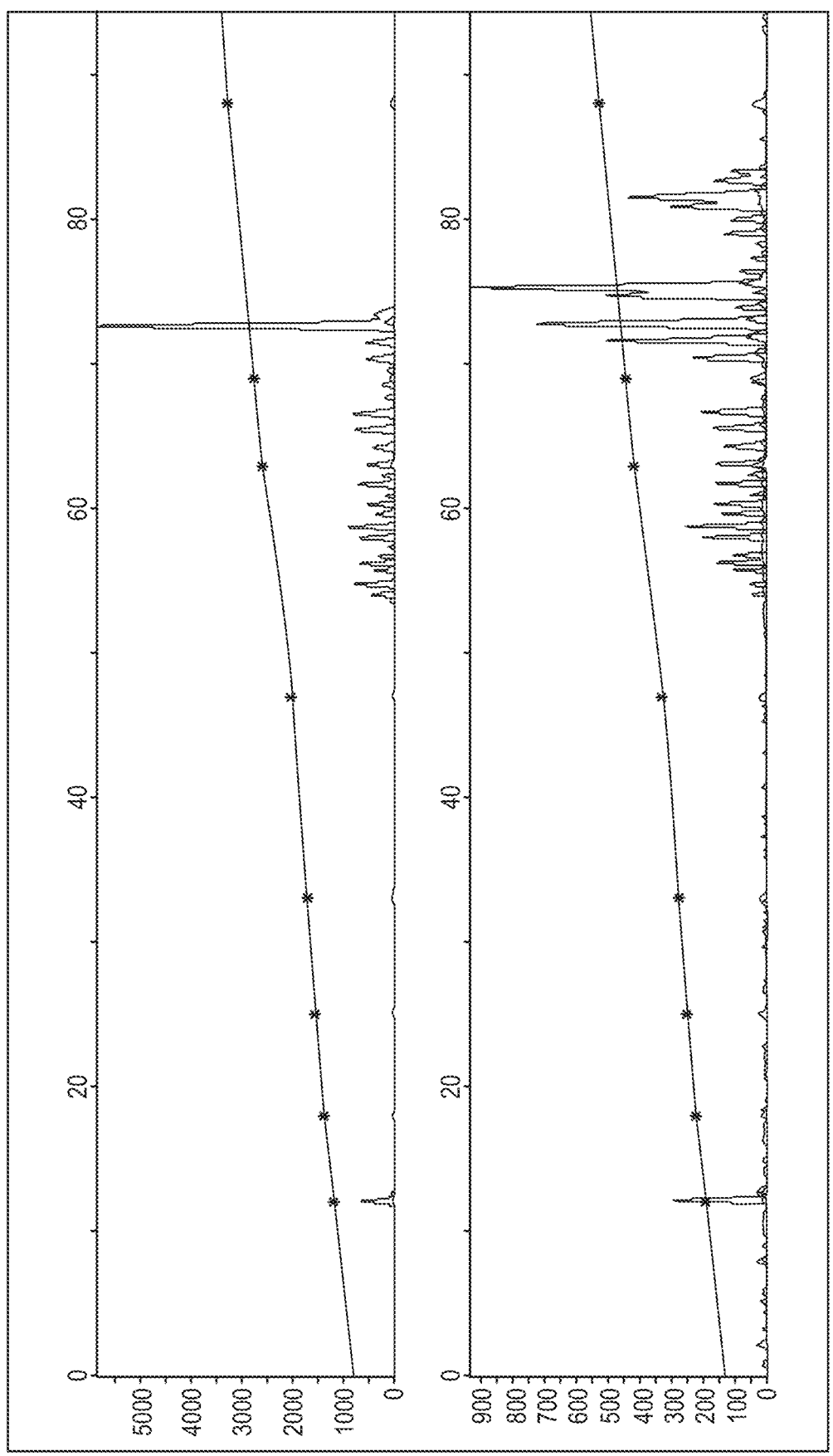

Additional comparisons were conducted for B primer damage in SNAPPs prepared by different methods in accordance to this disclosure. As depicted in FIG. 3F, SNAPPs made by different procedures such as, for example, water initiated SNAPPs, oil initiated SNAPPs, and Nanomi SNAPPs, show different patterns and different amounts of B primer damage. Experiments have shown that in the presence of dsDNA with a sufficiently high Tm, the polymerase falls off the extending primer, such that short DNA products are observed (data not shown). In the experiments shown herein, at the time that the dye labeled primer A is added in excess, the original template is still present, although the sample is heated to 95 C, it is possible that the polymerase fall offs in the B primer region are due to a tight binding B primer complement. In the experiment shown in FIG. 3G, as in previous versions of this assay shown in FIG. 2 and FIG. 3A-F, no short products are observed outside the B primer region in free extension reactions (no ddNTP's). In addition for BB340, the B primer was extended an additional 12 bases at the 5' end. At no time prior to the extension from the dye labeled primer A was there double stranded DNA for these 12 bases as the same template was used which only covered the 3' 30 bases. Thus the 12 bases past the full length product peak in the upper figure can only be due to polymerase fall off due to DNA damage. In a companion experiment, excess B primer complement was added with the dye labeled A primer and both were hybridized. In this experiment, it can be assumed that all B primers were double stranded, hybridized with complement. No change in pattern was observed (data not shown).

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and examples be considered as exemplary only, with a scope and spirit being indicated by the claims.

EXAMPLES

Example 1

Preparation of SNAPPs

The following materials were prepared for a production of 8% Acrylamide/10% Methylene Bisacrylamide Continuous oil phase (SNAPP oil or "SNOIL"): 730 mL TEGOSOFT DEC, 200 mL mineral oil, and 70 g Abil WE09 were combined to make 1 L in total volume (11.25 mL was used for the batch). The oil was not degassed or argon capped.

Initiator oil: 1 g AIBN was placed in a 50 mL glass bottle and 50 mL of degassed SNOIL was added. The bottle was capped with argon gas. A stir bar was added and stirred to suspend the AIBN in SNOIL for 7 minutes at maximum speed (1150 rpm) on a stir plate. The suspension was then spun down in a 250 mL centrifuge tube at maximum speed (approximately 3400 rpm or 1877 rcf) for 5 minutes. A total volume of 50 mL was produced (1.2 mL was used, drawn off the top). The oil was degassed and argon capped.

Aqueous gel reaction mixture ("SNAPP Mix" for 8% Acrylamide): 0.450 g acrylamide (AA) and 0.050 g bisacrylamide (BIS) were weighed and put into a 2 mL conical tube. 550 µL water was added and vortexed to dissolve which generated 1 mL of "5×10/10 solution". 208 µL of the 5×10/10 solution was added to 603 µL water. Separately, 2550 µL of deionized water was added to a tube with 10.22 µmol (2630 OD) of DNA. This resulted in 4 mM DNA solution (489 µL of 4 mM DNA was used for the batch). The SNAPP Mix was completed by combining 208 µL of the 5×10/10 solution with 603 µL water and 489 µL of the 4 mM DNA. This resulted in 1.30 mL total SNAPP Mix (1.25 mL was used for production). The gel reaction mixture was not degassed or argon capped.

SNAPP Buffer: 1× Tris-EDTA, 0.1% Triton X-100, and 0.02% $NaN_3$

Next, an emulsion was generated using an IKA® ULTRA TURRAX® Tube Drive (Model: UTTDS1) device. The SNOIL was stirred at least 5 min prior to using it.

11.25 mL non-degassed SNOIL was added to a 15 mL IKA tube. Then, 1.25 mL SNAPP Mix was added to the tube. The Turrax tube was placed on the Turrax tube drive at a speed of 5 for 5 minutes.

Then, the emulsion was polymerized by first putting 12 mL of the emulsion into a 25 mL biotage glass vial. Then, 1.2 mL of Initiator SNOIL was added to the vial under argon and sealed with an aluminum re-sealable septum cap using a crimper. A needle was used to flush the biotage vial with argon to prevent the presence of any oxygen. The vial was placed on the rotisserie, and the rotisserie placed in an oven preheated to 90° C. The vial and contents were heated for 40 minutes in the oven. The polymerized emulsion may then be placed in a 4° C. fridge overnight or, if immediate work up is desired, it may be placed into ice for 30 minutes.

The polymerized emulsion was centrifuged for 20 minutes at 4000 rpm. The supernatant was removed with a pipetteman, ensuring that the pellet was not disturbed. Then, 8 mL of butanol: 0.1% SDS (2:1) mix was added, and a new aluminum top was crimped. The mixture was vortexed to dissolve the pellet in the butanol: 0.1% SDS mix.

The dissolved solution was transferred to a 14 mL falcon tube, and 1 mL of 0.1% SDS was gently added. The tube was spun for 5 minutes at 3400 rpm or 1877 rcf. The butanol layer was removed with a pipette. 8 mL of 0.1% SDS solution was added to the 14 mL falcon tube and the pellet was re-suspended via vortexing.

The solution was transferred into a Nalgene tube.

The following steps were preformed to further isolate the product:
1. Fill the centrifuge tube with 0.1% SDS.
2. Spin down the centrifuge tube for 10 minutes at 15K rpm.
3. Pour out supernatant and remove white residue with spatula and kimwipe.
4. Add 0.1% SDS solution to fill the centrifuge tube and re-suspend the pellet via vortexing.
5. Spin down for 5 minutes at 15K rpm.
6. Repeat steps 1-4 one more time.
7. Pour out supernatant and remove white residue with spatula and kimwipe.
8. Add SNAPP buffer solution to fill the centrifuge tube and re-suspend the pellet via vortexing.
9. Spin down for 5 minutes at 15K rpm.

10. Pour out supernatant and remove white residue with spatula and kimwipe.
11. Repeat steps 7-9 one more time.
12. Add 8 mL of SNAPP buffer to each tube and re-suspend the pellet thoroughly.
13. Transfer into a new 14 mL falcon tube.
14. Subtract the volume of the contents from 12.5 mL and add this amount of SNAPP buffer to the tube.
15. Vortex the tube and add the contents to the same 14 mL falcon tube.
16. Ensure the total volume in the falcon tube is 12.5 mL by adding extra SNAPP buffer if used.
17. Label the container with appropriate batch number.
18. Refrigerate at 4° C. for storage.

The procedure was repeated 15 times using the emulsion and initiator volumes and polymerization times set forth in Table 3 below.

TABLE 3

| Batch | Emulsion Vol. | Initiator Vol. | Polymerization Time (H) | Vol. % Initiator |
|---|---|---|---|---|
| 1 | 12 | 12 | 2 | 100 |
| 2 | 12 | 6 | 2 | 50 |
| 3 | 12 | 3 | 2 | 25 |
| 4 | 12 | 1.2 | 2 | 10 |
| 5 | 12 | 0.6 | 2 | 5 |
| 6 | 12 | 0.3 | 2 | 2.5 |
| 7 | 12 | 0.12 | 2 | 1 |
| 8 | 10 | 1 | 2 | 10 |
| 9 | 12 | 12 | 1 | 100 |
| 10 | 12 | 6 | 1 | 50 |
| 11 | 12 | 3 | 1 | 25 |
| 12 | 12 | 1.2 | 1 | 10 |
| 13 | 12 | 0.6 | 1 | 5 |
| 14 | 12 | 0.3 | 1 | 2.5 |
| 15 | 12 | 0.12 | 1 | 1 |
| 16 | 10 | 1 | 1 | 10 |

Figure 4:
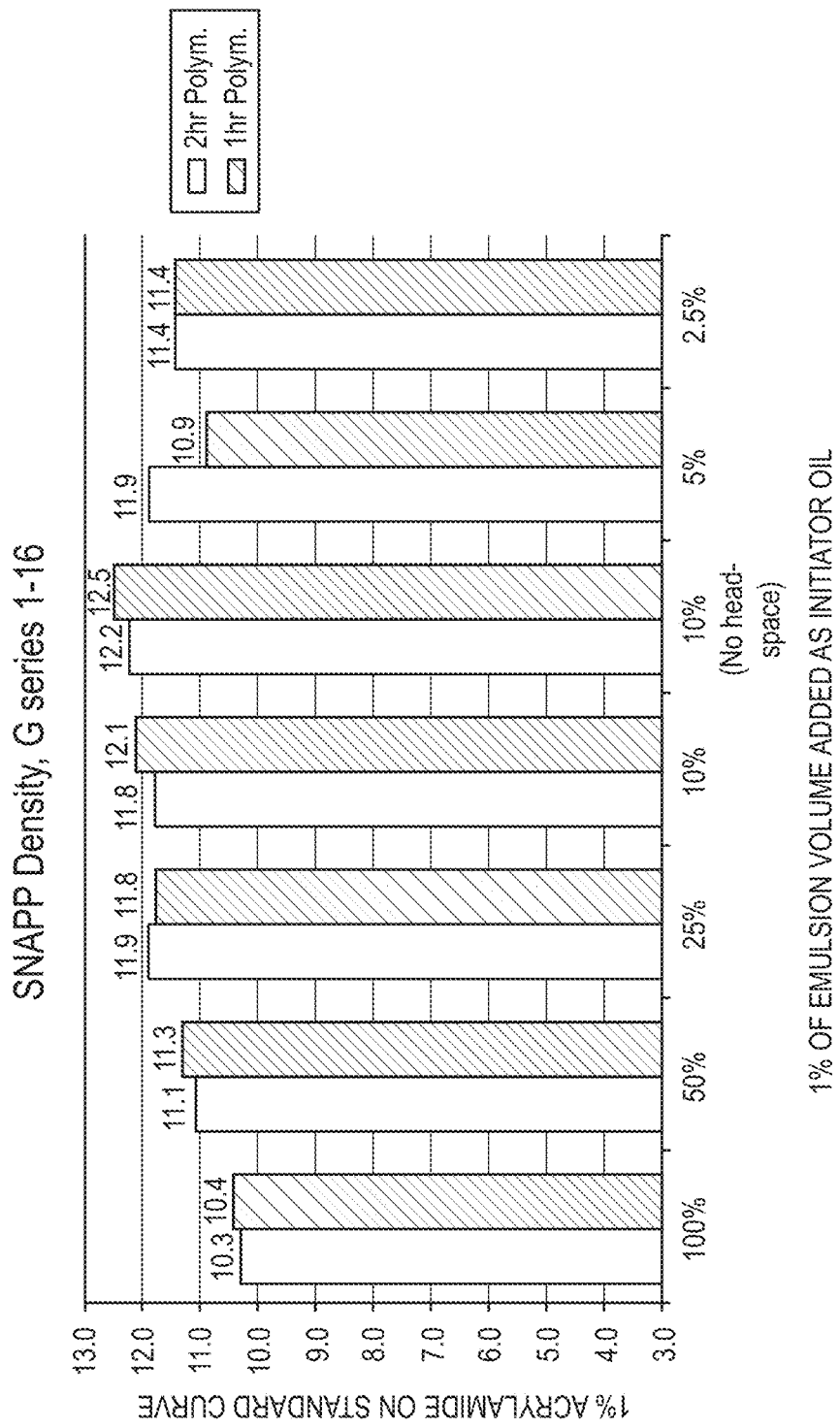
FIG. 4 depicts the SNAPP density for the products described in the disclosure.

All batches successfully polymerized except for batches 7 and 15, which had an initiator concentration of 1 vol %. Of the polymerized batches, all yielded a SNAPP density of between 10% and 13% as represented in FIG. 4

Example 2

Evaluation of Damage to DNA Attached to a Surface

The following protocol and methods were followed to prepare assays for quantifying and comparing primer damage. This protocol is designed to evaluate the effect of coupling an oligo to a surface, whether a bead (SNAPP) or a flat surface like a slide or chip. The type of damage depends on the method by which the DNA was coupled to the particular surface. With acrylamide polymerization and the release of free oxygen radicals, severe DNA damage may be expected including the formation of abasic sites and modified nucleotides. If beads are formed independent of DNA coupling and the oligonucleotide attached secondarily the damage may be primarily the coupling of the DNA to the surface through exocyclic amines.

Materials: The following oligos are used for the assay: A template with a sequence at the 3' end complementary to the sequence of the oligonucleotide on the surface; A sequencing oligo which is dye labeled (Fam) at the 5' end and which is complementary to the 5' end of the template.

Reagents: Ion Torrent Annealing buffer, 25 mM MgCl2, dNTP's at 1 mM and 100 µM.

Polymerases: GeneAmp High Fidelity Enzyme Mix (AB #4328216), Ion Torrent Sequencing Polymerase 1.0.

Protocol: The amount of starting material depends on the expected density of the oligonucleotide on the surface to be analyzed. For SNAPPs, 200,000 SNAPPs are used per assay. The appropriate SNAPPs are transferred to a 0.2 mL microcentrifuge tube and 1 µM final concentration of template is added. The volume is adjusted to 10 µL with Ion Torrent Annealing Buffer. The samples are thermocycled for 2 minutes at 95 C and 2 min at 37 C to allow hybridization of the template to the surface bound oligo. SNAPP samples are centrifuged at 15,000 RPM for 3 minutes to pellet the SNAPPs and the supernatant is carefully removed. Extension of the surface primer is carried out by the addition of 200 µM dNTP's with 5 mM Mg+2 in a total volume of 10 µL. The volume is made up with annealing buffer or other polymerase compatible buffer. 0.5 unit of polymerase is added and the reaction is heated to 60 C for 30 minutes in a thermocycler and at the end cooled to 4 C. SNAPP samples are again centrifuged at 15,000 RPM for 3 min to pellet the SNAPPs and the supernatant is carefully removed. Dye labeled sequencing oligo is added at 1 µM final concentration in a total volume of 10 µL of annealing buffer and the samples are thermocylcled for 2 minutes at 95 C and 2 minutes at 37 C to allow hybridization of the primer to the extended surface template. SNAPP samples are again centrifuged at 15,000 RPM for 3 minutes to pellet the SNAPPs and the supernatant is removed. Ion Torrent Sequencing Polymerase 1.0 (1 unit) is added with 5 mM Mg+2 in a total volume of 10 µL of annealing buffer. Sample is allowed to sit at room temperature for 15 minutes. SNAPP samples are centrifuged at 15,000 RPM for 3 minutes and the supernatant is removed. dNTP's at 20 µM final concentration with 5 mM Mg+2 in a total volume of 10 µL of annealing buffer is added to the SNAPP sample and the sample is incubated for 30 minutes at 37 C to extend the dye labeled primer. At the end of the extension time the sample is held at 4 C. SNAPP samples are centrifuged at 15,000 RPM for 3 minutes and the supernatant is removed. HiDiFormamide (AB #4311320) (20 µL) is added to the SNAPPs and the sample is heated to 95 C for 5 minutes. SNAPP samples are centrifuged at 15,000 RPM for 3 minutes to pellet the SNAPPs. The formamide sample is transferred to a microtiter plate and the plate inserted into an AB 3130 for electrophoretic separation of the DNA fragments and analysis.

The electrophoretic data is analyzed with Peak Scanner (AB). The concentration of the extension products are adjusted such that the full length extension peak is between 5000 and 7500 (full scale), but not off scale. Baseline is set at 50 units such that peaks smaller than 50 units (1% or less of the full length extension product) are not measured (this setting may be adjusted). Two measurements are made on the electrophoretic data; 1. The average peak height of the extension failures as a percent relative to the full length extension product, and 2. The total percent of the extension failures relative to the full length extension product. From the Peak Scanner software, the height of each peak above the baseline setting can be obtained. The average height of the peaks, other than the full length extension peak, above the base line setting, is determined and divided by the height of the full length extension peak. This value is then multiplied by the number of peaks above the baseline to obtain the total percent of the extension failures. The results from this protocol are depicted in FIGS. 2A-D.

Example 3

Evaluation of Progress of Polymerization Over Time

Figure 5A:
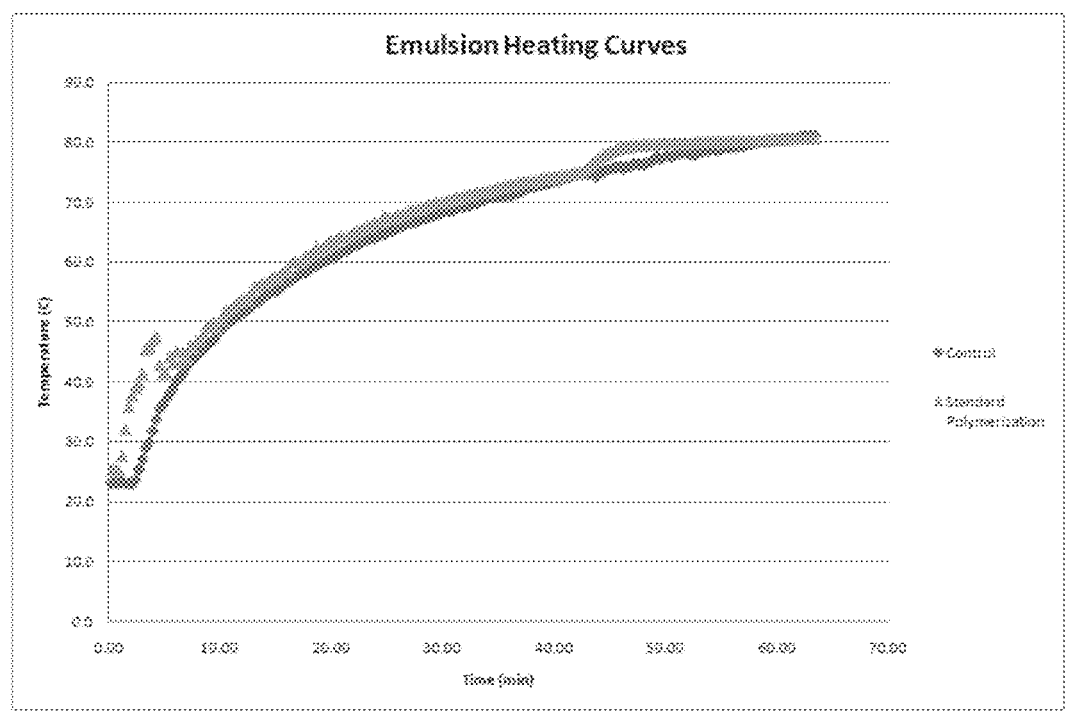
FIGS. 5A-B depict the result of analyses performed on emulsion-based polymerizations during SNAPP synthesis.

FIG. 5A depicts curves obtained by observing emulsions, made approximately according to Example 1, where a temperature probe was inserted into the emulsion and readings were taken at regular intervals. The "control" emulsion was comprised of just water in SNOIL while the "standard polymerization" emulsion contained the aqueous components used to make SNAPPs as described in Example 1. As depicted in FIG. 5A, after approximately 45 minutes there was a spike in the temperature of the standard polymerization which was not manifested in the control emulsion.

Figure 5B:
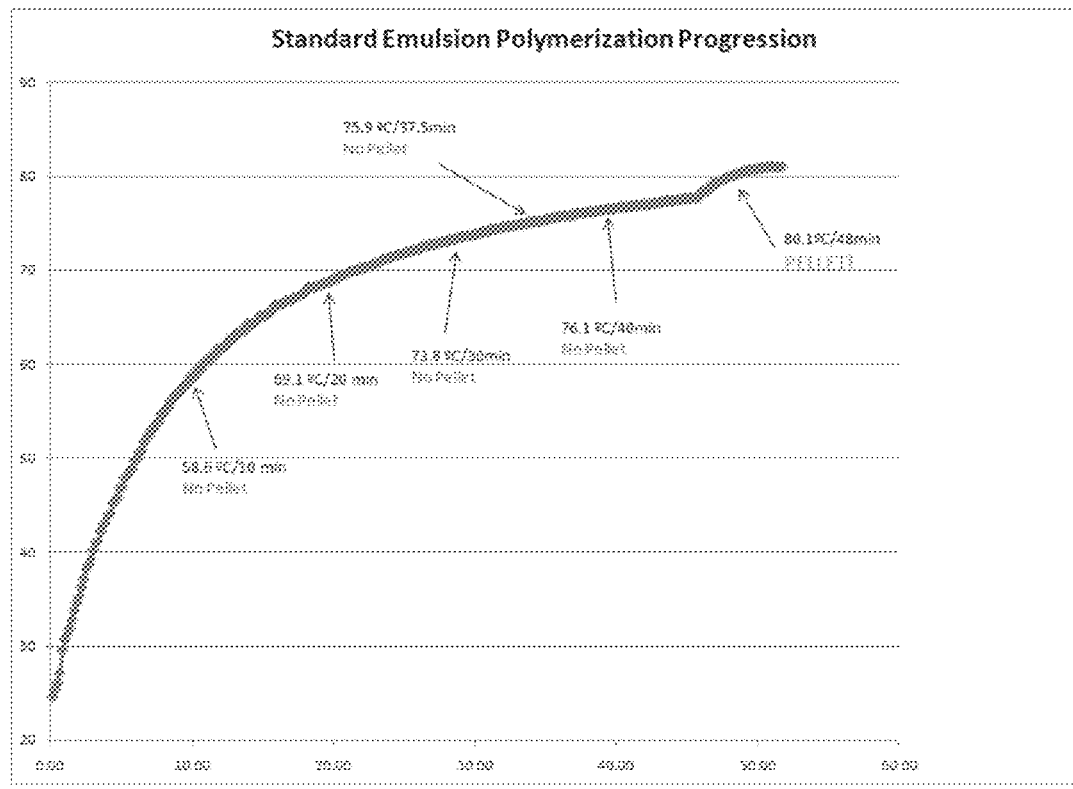

FIG. 5B depicts the results of an assay in which the same assay depicted in FIG. 5A was repeated, where aliquots of the emulsion were taken at the time points indicated by the arrows. Each aliquot of the emulsion was broken to extract the contents of the aqueous, disperse phase and then centrifuged. Lack of pellet formation upon centrifugation indicated that no polymerization had taken place; conversely, the formation of an observable pellet indicated a the formation of polymerized particles. The sudden appearance of the pellet comprised of polymerized particles correlated with the onset of the temperature spike in the heating curve.

In a first aspect, a method of making polymer particles includes making an aqueous gel reaction mixture, forming an emulsion comprising dispersed aqueous phase micelles of gel reaction mixture in a continuous phase, adding an initiator oil comprising at least one polymerization initiator to the continuous phase, and performing a polymerization reaction in the micelles, wherein the initiator oil is present in a volume % relative to a volume % of the gel reaction mixture of between about 1 vol % to about 20 vol %.

In an example of the first aspect, the initiator oil is present in a volume % relative to a volume % of the gel reaction mixture of between about 2 vol % to about 10 vol %.

In another example of the first aspect and above examples, the polymer particles are polyacrylamide polymer particles.

In a further example of the first aspect and above examples, the polymerization initiator is azobisisobutyronitrile (AIBN).

In an additional example of the first aspect and above examples, the method yields a polymer particle packed density of at least about 5%.

In another example of the first aspect and above examples, the method further includes quenching the polymerization reaction upon completion of the reaction.

In a second aspect, a method of making polymer particles includes making an aqueous gel reaction mixture, forming an emulsion comprising dispersed aqueous phase micelles of gel reaction mixture in a continuous phase, adding an initiator oil comprising at least one polymerization initiator to the continuous phase, performing a polymerization reaction in the micelles, and quenching the polymerization reaction upon completion of the reaction.

In an example of the second aspect, the polymerization reaction is quenched immediately after completion of the reaction.

In another example of the second aspect and above examples, the initiator oil is present in a volume % relative to a volume % of the gel reaction mixture of between about 1 vol % to about 20 vol %.

In a further example of the second aspect and above examples, the polymer particles are polyacrylamide polymer particles.

In an additional example of the second aspect and above examples, the polymerization initiator is azobisisobutyronitrile (AIBN).

In another example of the second aspect and above examples, the method yields a polymer particle packed density of at least about 5%.

In a third aspect, a method of making scaffolded nucleic acid polymer particles ("SNAPPs") includes making an aqueous gel reaction mixture comprising a nucleic acid fragment, forming an emulsion comprising dispersed aqueous phase micelles of gel reaction mixture in a continuous phase, adding an initiator oil comprising at least one polymerization initiator to the continuous phase, and performing a polymerization reaction in the micelles, wherein the initiator oil is present in a volume % relative to a volume % of the gel reaction mixture of between about 1 vol % to about 20 vol %.

In an example of the third aspect, the method further includes quenching the polymerization reaction upon completion of the reaction.

In another example of the third aspect and above examples, the SNAPPs produce a sequencing product having an average B primer region relative to a full length of the sequencing product that is less than about 2%.

In a further example of the third aspect and above examples, the initiator oil is present in a volume % relative to a volume % of the gel reaction mixture of between about 2 vol % to about 10 vol %.

In an additional example of the third aspect and above examples, the SNAPPs are polyacrylamide polymer particles.

In another example of the third aspect and above examples, the polymerization initiator is azobisisobutyronitrile (AIBN).

In a further example of the third aspect and above examples, the method yields a SNAPP density of at least about 10%.

In a fourth aspect, a method of making scaffolded nucleic acid polymer particles ("SNAPPs") includes making an aqueous gel reaction mixture comprising a nucleic acid fragment, forming an emulsion comprising dispersed aqueous phase micelles of gel reaction mixture in a continuous phase, adding an initiator oil comprising at least one polymerization initiator to the continuous phase, performing a polymerization reaction in the micelles, and quenching the polymerization reaction upon completion of the reaction.

In an example of the fourth aspect, the polymerization reaction is quenched immediately after completion of the reaction.

In another example of the fourth aspect and above examples, the initiator oil is present in a volume % relative to a volume % of the gel reaction mixture of between about 1 vol % to about 20 vol %.

In a further example of the fourth aspect and above examples, the SNAPPs are polyacrylamide polymer particles.

In an additional example of the fourth aspect and above examples, the polymerization initiator is azobisisobutyronitrile (AIBN).

In another example of the fourth aspect and above examples, the method yields a SNAPP packed density of at least about 5%.

In a fifth aspect, a scaffolded nucleic acid polymer particle ("SNAPP") is obtained by a method including making an aqueous gel reaction mixture comprising a nucleic acid fragment, forming an emulsion comprising dispersed aqueous phase micelles of gel reaction mixture in a continuous phase, adding an initiator oil comprising at least one polymerization initiator to the continuous phase, and performing a polymerization reaction in the micelles, wherein the initiator oil is present in a volume % relative to a volume % of the gel reaction mixture of between about 1 vol % to about 20 vol %.

In an example of the fifth aspect, the initiator oil is present in a volume % relative to a volume % of the gel reaction mixture of between about 2 vol % to about 10 vol %.

In another example of the fifth aspect and above examples, the SNAPPs produce a sequencing product having an average B primer region relative to a full length of the sequencing product that is less than about 2%.

In a further example of the fifth aspect and above examples, the SNAPPs are polyacrylamide polymer particles.

In an additional example of the fifth aspect and above examples, the polymerization initiator is azobisisobutyronitrile (AIBN).

In a sixth aspect, a scaffolded nucleic acid polymer particle ("SNAPP") is obtained by a method including making an aqueous gel reaction mixture comprising a nucleic acid fragment, forming an emulsion comprising dispersed aqueous phase micelles of gel reaction mixture in a continuous phase, adding an initiator oil comprising at least one polymerization initiator to the continuous phase, performing a polymerization reaction in the micelles, and quenching the polymerization reaction upon completion of the reaction.

In an example of the sixth aspect, the polymerization reaction is quenched immediately after completion of the reaction.

In another example of the sixth aspect and above examples, the initiator oil is present in a volume % relative to a volume % of the gel reaction mixture of between about 1 vol % to about 20 vol %.

In a further example of the sixth aspect and above examples, the SNAPPs produce a sequencing product having an average B primer region relative to a full length of the sequencing product that is less than about 2%.

In an additional example of the sixth aspect and above examples, the SNAPPs are polyacrylamide polymer particles.

In another example of the sixth aspect and above examples, wherein the polymerization initiator is azobisisobutyronitrile (AIBN).

In a seventh aspect, a method of evaluating the effect of coupling an oligo to a surface includes preparing an assay comprising one or more oligos, one or more reagents, and one or more polymerases, conducting an electrophoretic separation of the DNA fragments for analysis analyzing the electrophoretic data.

In an example of the seventh aspect, the oligos are 1) a template with a sequence at the 3' end complementary to the sequence of the oligonucleotide on the surface and 2) a sequencing oligo which is dye labeled (Fam) at the 5' end and which is complementary to the 5' end of the template.

In another example of the seventh aspect and above examples, the reagents are Ion Torrent Annealing buffer, 25 mM MgCl2, dNTP's at 1 mM and 100 µM.

In a further example of the seventh aspect and above examples, the polymerase is GeneAmp High Fidelity Enzyme Mix (AB #4328216).

In an additional example of the seventh aspect and above examples, the polymerase is Ion Torrent Sequencing Polymerase 1.0.

In an eighth aspect, a method for detecting extension of a primer includes forming a primer:template duplex by contacting a surface-linked primer with a nucleic acid template under conditions where the surface-linked primers hybridizes to the nucleic acid template to form the primer:template duplex; extending the surface-linked primer of the primer:template duplex, thereby forming an extended surface-linked primer; forming a primer:primer duplex by contacting the extended surface-linked primer with a labeled primer under conditions where the labeled primer hybridizes to the extended surface primer, thereby forming the primer:primer duplex; extending the labeled primer of the primer:primer duplex, thereby forming an extended labeled primer; and detecting the label of the extended labeled primer.

In a ninth aspect, a method for determining the relative proportion of one or more primer extension products within a population of primer extension products includes forming a plurality of primer:template duplexes by contacting a plurality of surface-linked primers with a plurality of nucleic acid templates under conditions where at least two of the surface-linked primers hybridize to different nucleic acid templates; extending the surface-linked primer of at least two of the plurality of primer:template duplexes, thereby forming a plurality of surface-linked extended primers; forming a plurality of primer:primer duplexes by contacting at least some of the plurality of extended surface-linked primers with a plurality of labeled primers under conditions where at least two of the extended surface-linked primers hybridize to different labeled primers; extending the labeled primer of at least two of the plurality of primer:primer duplexes, thereby forming a population of extended labeled primers; and separating at least two different members of the population of extended labeled primers from each other.

In an example of the ninth aspect, the method further includes separately detecting the at least two different members after the separating. In an example, the at least two different members of the population include a first extended labeled primer and a second extended labeled primer, and the method further includes separately detecting the label of the first extended labeled primer and the label of the second extended labeled primer.

In another example of the ninth aspect and above examples, the population includes a first extended labeled primer and the method further includes determining the amount of the first extended labeled primer based on the total amount of signal detected from the label of the first extended labeled primer. In an example, the population further includes a second extended labeled primer and the method further includes determining the amount of the second extended labeled primer based on the total amount of signal detected from the label of the second extended labeled primer.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of making polymer particles, said method comprising:
    making an aqueous gel reaction mixture including an acrylamide or derivative thereof monomer and including a nucleic acid fragment;
    forming an emulsion comprising dispersed aqueous phase micelles of gel reaction mixture in a continuous phase;
    adding an initiator oil comprising at least one polymerization initiator to the continuous phase; and
    performing a polymerization reaction in the micelles to form polymer particles conjugated to the nucleic acid fragment;
    wherein the initiator oil is present in a volume % relative to a volume % of the gel reaction mixture of between about 1 vol % to about 20 vol %.

2. The method of claim 1, wherein the initiator oil is present in a volume % relative to a volume % of the gel reaction mixture of between about 2 vol % to about 10 vol %.

3. The method of claim 1, wherein the polymer particles are polyacrylamide polymer particles.

4. The method of claim 1, wherein the polymerization initiator is azobisisobutyronitrile (AIBN).

5. The method of claim 1, wherein the method yields a polymer particle packed density of at least about 5%.

6. The method of claim 1, further comprising quenching the polymerization reaction upon completion of the reaction.

7. The method of claim 1, wherein the aqueous gel reaction mixture further includes a crosslinker.

8. The method of claim 7, wherein the crosslinker is a diacrylamide.

9. The method of claim 7, wherein the crosslinker is included in a range of 5% to 20% relative to the total monomer content.

10. The method of claim 1, wherein the amount of monomer in the aqueous gel reaction mixture is sufficient to provide a total monomer content in the polymer particles in a range of 3% to 20%.

11. The method of claim 1, wherein the range is 5% to 10%.

12. The method of claim 1, wherein the polymer particles have an average particle size of less than 5 micrometers.

13. The method of claim 12, wherein the polymer particles have an average particle size of less than 1.5 micrometers.

14. The method of claim 12, wherein the polymer particles have a coefficient of variance of less than 20%.

15. The method of claim 1, wherein the initiator oil includes a diethylhexyl carbonate.

16. The method of claim 1, wherein the initiator oil includes mineral oil.

17. The method of claim 1, wherein performing the polymerization reaction includes heating the emulsion to a temperature of at least 50° C. while maintaining the emulsion.

18. The method of claim 1, further comprising quenching the polymerization reaction following performing the polymerization reaction.

19. The method of claim 17, wherein quenching the polymerization reaction includes cooling the emulsion to a temperature not greater than room temperature.

20. The method of claim 17, wherein quenching the polymerization reaction includes cooling in an ice bath or a freezer.

* * * * *